United States Patent
Jansson et al.

(10) Patent No.: US 10,328,192 B2
(45) Date of Patent: Jun. 25, 2019

(54) RELATIVE PUMP CALIBRATION FOR ULTRAFILTRATION CONTROL IN A DIALYSIS APPARATUS

(71) Applicant: GAMBRO LUNDIA AB, Lund (SE)

(72) Inventors: Olof Jansson, Vellinge (SE); Christian Vartia, Veberod (SE)

(73) Assignee: GAMBRO LUNDIA AB, Lund (SE)

( * ) Notice: Subject to any disclaimer, the term of this patent is extended or adjusted under 35 U.S.C. 154(b) by 556 days.

(21) Appl. No.: 14/904,307

(22) PCT Filed: Jul. 9, 2014

(86) PCT No.: PCT/EP2014/064744
§ 371 (c)(1),
(2) Date: Jan. 11, 2016

(87) PCT Pub. No.: WO2015/007596
PCT Pub. Date: Jan. 22, 2015

(65) Prior Publication Data
US 2016/0151554 A1    Jun. 2, 2016

(30) Foreign Application Priority Data

Jul. 15, 2013  (SE) ...................................... 1350878

(51) Int. Cl.
*A61M 1/16*   (2006.01)
*A61M 1/34*   (2006.01)
(Continued)

(52) U.S. Cl.
CPC ............ *A61M 1/1601* (2014.02); *A61M 1/16* (2013.01); *A61M 1/165* (2014.02);
(Continued)

(58) Field of Classification Search
None
See application file for complete search history.

(56) References Cited

U.S. PATENT DOCUMENTS

| 4,267,040 A | 5/1981 | Schal |
| 4,275,726 A | 6/1981 | Schael |

(Continued)

FOREIGN PATENT DOCUMENTS

| CN | 101347644 | 1/2009 |
| CN | 102389593 | 3/2012 |

(Continued)

OTHER PUBLICATIONS

International Search Report; PCT/EP2014/064763—dated Sep. 16, 2014—3 pages.

(Continued)

*Primary Examiner* — Richard C Gurtowski
(74) *Attorney, Agent, or Firm* — K&L Gates LLP

(57) ABSTRACT

A control unit (30) is arranged to control a dialysis fluid distribution system (12) comprising two volumetric pumps (P1, P2) and a dialyzer (13). The control unit (30) is operable in a calibration mode, to establish a bypass flow path that bypasses the dialyzer (13) and extends between the pumps (P1, P2) and to operate the pumps (P1, P2) at first and second calibration speeds so as to balance the flow rates generated by the pumps (P1, P2), e.g. based on a measured pressure or fluid level in dialysis fluid distribution system (12). The control unit (30) determines, based on the first and second calibration speeds, a relation between the stroke volumes of the pumps (P1, P2). The control unit (30) is further operable in a treatment mode, to establish a main flow path that extends between the first and second pumps (P1, P2) via the dialyzer (13) and to control the first and second pumps (P1, P2), based on the relation between their stroke volumes, to operate at a respective treatment frequency so as to generate a selected ultrafiltration rate in the dialyzer (13).

27 Claims, 10 Drawing Sheets

(51) Int. Cl.
*F04B 13/00* (2006.01)
*F04B 23/06* (2006.01)
*F04B 49/06* (2006.01)
*F04B 51/00* (2006.01)
*G05B 15/02* (2006.01)

(52) U.S. Cl.
CPC ........ *A61M 1/1645* (2014.02); *A61M 1/1647* (2014.02); *A61M 1/34* (2013.01); *F04B 13/00* (2013.01); *F04B 23/06* (2013.01); *F04B 49/065* (2013.01); *F04B 51/00* (2013.01); *G05B 15/02* (2013.01); *A61M 2205/12* (2013.01); *A61M 2205/3334* (2013.01); *A61M 2205/52* (2013.01); *A61M 2205/70* (2013.01); *A61M 2205/702* (2013.01)

(56) References Cited

U.S. PATENT DOCUMENTS

| | | |
|---|---|---|
| 4,334,988 A | 6/1982 | Milligan |
| 4,585,552 A | 4/1986 | Gummesson et al. |
| 4,747,950 A | 5/1988 | Guinn |
| 4,769,001 A | 9/1988 | Prince |
| 5,247,434 A | 9/1993 | Peterson |
| 5,954,951 A | 9/1999 | Nuccio |
| 6,331,252 B1 | 12/2001 | El Sayyid et al. |
| 6,691,047 B1 | 2/2004 | Fredericks |
| 2007/0243990 A1 | 10/2007 | Kolenbrander et al. |
| 2008/0093276 A1 | 4/2008 | Roger et al. |
| 2008/0105600 A1 | 5/2008 | Connell et al. |
| 2009/0124963 A1 | 5/2009 | Hogard et al. |
| 2009/0008331 A1 | 9/2009 | Wilt et al. |
| 2011/0132838 A1 | 6/2011 | Curtis |
| 2012/0145615 A1 | 6/2012 | Rohde et al. |
| 2012/0193290 A1 | 8/2012 | Breuel et al. |
| 2012/0267309 A1 | 10/2012 | Peters et al. |
| 2012/0305090 A1 | 12/2012 | Bernard |
| 2013/0020237 A1 | 1/2013 | Wilt et al. |

FOREIGN PATENT DOCUMENTS

| | | |
|---|---|---|
| DE | 69007342 | 9/1994 |
| DE | 10112848 | 9/2001 |
| WO | 9200768 | 1/1992 |
| WO | 2007118235 | 10/2007 |
| WO | 2013019994 | 2/2013 |

OTHER PUBLICATIONS

Written Opinion; PCT/EP2014/064763—dated Sep. 16, 2014—7 pages.
International Search Report; PCT/EP2014/064744; dated Sep. 16, 2014; 6 pages.
Written Opinion; PCT/EP2014/064744; dated Sep. 16, 2014; 8 pages.

RELATIVE PUMP CALIBRATION FOR ULTRAFILTRATION CONTROL IN A DIALYSIS APPARATUS

CROSS-REFERENCE TO RELATED APPLICATIONS

The present application is a National Phase of International Application No. PCT/EP2014/064744, filed on Jul. 9, 2014, which claims priority to Sweden Patent Application No. 1350878-3, filed Jul. 15, 2013, the entire contents of each of which are incorporated herein by reference and relied upon.

TECHNICAL FIELD

The present invention relates to a technique for controlling ultrafiltration in connection with dialysis, and in particular to a technique for calibrating one or more volumetric pumps for pumping a dialysis fluid through a dialyzer in a dialysis apparatus.

BACKGROUND ART

In treating chronic renal failure, various methods of purification and treatment of blood with machinery are used to replace the function of a healthy kidney. Such methods aim at withdrawing fluid and removing substances from the blood, and they may also involve adding fluid and substances to the blood. Such purification and treatment may be performed by pumping a dialysis fluid through a blood filtration unit, commonly denoted a dialyzer, in which fluid and substances are transported over a semi-permeable membrane. Diffusive mass transport through the membrane is predominant in hemodialysis (HD), whereas hemofiltration (HF) uses mainly convective mass transport through the membrane. Hemodiafiltration (HDF) is a combination of the two methods.

The withdrawal of fluid in the dialyzer, also known as ultrafiltration, is given by the difference between the spent dialysis fluid pumped out of the dialyzer and the fresh dialysis fluid pumped into the dialyzer. Because of the large volume of dialysis fluid that is exposed to the membrane in the dialyzer during a dialysis treatment, there is a need for accurate control of the ultrafiltration. Taking hemodialysis as an example, typically about 200 liters of dialysis fluid are passed through the dialyzer during a treatment session. The target amount of ultrafiltrate during a treatment session is typically about 2 to 3 liters and may need to be controlled with a maximum deviation of the order of only 0.1 to 0.2 liter. Accordingly, in this example, ultrafiltration may need to be controlled with a maximum error of approximately 1:1000 in relation to the total flow of dialysis fluid.

There are different prior art techniques for achieving accurate control of ultrafiltration in a dialysis apparatus.

U.S. Pat. No. 4,267,040 discloses a dialysis apparatus having a passive balancing device. The balancing device consists of two chambers, each being subdivided by a displaceable element and having an inlet line for fresh dialysis fluid and an outlet line connected to a drain for spent dialysis fluid. Cutoff valves driven and switched by a control unit are arranged in the inlet and outlet lines. A pump is provided between the dialyzer and the balancing device to convey the dialysis fluid. The balancing device is operated in such a way that fresh dialysis fluid is supplied from a dialysis fluid source to the two balancing chambers in alternation through appropriate switching of the cutoff valves in the inlet lines. At the same time, fresh dialysis fluid is supplied from an already filled space of the other balance chamber to the dialyzer. The spent dialysis fluid from the dialyzer is pumped into the second space of the same balance chamber, from which the spent dialysis fluid then goes into an outlet. The part of the liquid circuit enclosed between the balancing device and the dialyzer behaves like a closed, constant-volume system. The ultrafiltration in the dialyzer, i.e. the amount of fluid that passes from the blood side to the dialysis fluid side of the dialyzer membrane, is controlled by a dedicated filtration pump which is connected for controlled removal of fluid from the system.

A dialysis apparatus equipped with this type of balancing device has a number of disadvantages. For one, the switching of the balancing chambers may produce audible noise to the discomfort of the patient undergoing dialysis and also the caretakers. Audible noise may be highly undesirable in a clinic setting as well as in a home setting. Further, the cutoff valves that control the switching will be subjected to significant mechanical load over time and may start to leak dialysis fluid as result of wear and fatigue. Any such leaks will produce errors in the resulting ultrafiltration. Still further, errors in the dedicated filtration pump will have a significant impact on the accuracy of the ultrafiltration, and it may be necessary to take measures to carefully control and supervise the operation of the filtration pump.

In this context, DE69007342 discloses a technique for calibrating a filtration pump, which is a volumetric pump that has either a rotor or a diaphragm for displacing the dialysis fluid. The pump is equipped with a pulse generator which emits pulses that represent a certain angle of rotation of the rotor or a certain displacement of the diaphragm and correspond to a certain quantity of dialysis fluid. During regular operation, the flow rate of the filtration pump is determined by dead reckoning, i.e. by counting the number of pulses emitted and applying a known correspondence between the number of pulses and the quantity of liquid pumped. This correspondence is determined in a calibration procedure, in which the pumped liquid is switched into a reservoir of exactly known capacity. By counting the number of pulses emitted in order to fill the reservoir, the exact correspondence between the number of impulses emitted and the quantity of liquid pumped can be determined.

The prior art also comprises U.S. Pat. No. 4,747,950 which is designed to balance the flow of dialysis fluid into the dialyzer, generated by an upstream pump, with the flow of dialysis fluid out of the dialyzer, generated by a downstream pump, and to achieve ultrafiltration by withdrawing a controlled amount of dialysis fluid from a location either upstream or downstream of the dialyzer. The disclosed dialysis fluid supply system contains a large number of pumps, in addition to the upstream and downstream pumps, and involves a complex distribution of dialysis fluid between and within different receptacles in the system. To ensure a balanced flow, a calibration procedure is implemented, in which the dialyzer is temporarily by-passed such that the dialysis fluid is pumped from the upstream pump through a calibration chamber to the downstream pump. The calibration chamber has a sight tube allowing the level of dialysis fluid to be visually inspected. The flow rate of the upstream pump is controlled in relation to the flow rate of the downstream pump until the level of dialysis fluid remains at a constant level in the sight tube.

Other techniques for ultrafiltration control by balancing the flow rates of fresh and spent dialysis fluid are e.g. known from US2012/0193290, US2011/0132838, US2008/0105600, US2002/0088752, US2012/0279910 and US2010/0016777.

Another approach to control the ultrafiltration during dialysis is to install one or more pumps upstream of the dialyzer and one or more pumps downstream the dialyzer in the dialysis fluid supply system and to relatively control the flow rates of the upstream and downstream pumps to achieve a desired ultrafiltration rate. This type of control requires accurate and continuous measurements of the flow rates of dialysis fluid into and out of the dialyzer, and one or more advanced flow meters are installed in the dialysis fluid supply system to provide this information. An example of a flow meter capable of continuously measuring the difference between the dialysis fluid flows into and out of the dialyzer is known from U.S. Pat. No. 4,585,552. A dialysis apparatus based on this approach may produce significantly less audible noise than a dialysis device with a balancing device. Further, since the ultrafiltration is controlled based on the readings of one or more flow meters, ultrafiltration may be largely unaffected by leaks in the dialysis fluid supply system, as long as the flow meter(s) operate correctly. However, flow meters with the required accuracy and precision may be quite costly and complex. It is also vital that the flow meters operate correctly over a long time of use. Techniques for calibrating the flow meters in this context are e.g. known from U.S. Pat. No. 6,331,252 and US2012/0145615.

The prior art also comprises US2007/0243990 which is unrelated to ultrafiltration control and discloses an apheresis system in which blood is removed from a donor, directed to a blood component separation device, such as a centrifuge, which collects one or more blood components (e.g. red blood cells, white blood cells, platelets or plasma), whereupon the remainder is returned to the donor. US2007/0243990 proposes a calibration procedure for relatively calibrating pairs of pumps in the apheresis system. During the calibration procedure, the pumps are alternately activated so that one pump is operated to increase the fluid level in a reservoir from an initial level, and then the other pump is operated to decrease the fluid level back to the initial level in the reservoir. A pump volume ratio between the pumps is given by the number of strokes performed by the respective pump while filling and emptying the reservoir. The pump volume ratio is stated to be useful for increasing the effectiveness and efficiency of the donation process. Another technique for relative pump calibration in the context of apheresis for blood plasma filtering and/or platelet separation is known from U.S. Pat. No. 4,769,001.

SUMMARY

It is an objective of the invention to at least partly overcome one or more limitations of the prior art.

One objective is to provide an alternative technique of controlling ultrafiltration in a dialysis apparatus.

Another objective is to provide a simple, accurate and robust technique of controlling ultrafiltration in a dialysis apparatus.

A still further objective is to enable a silent dialysis apparatus.

One or more of these objectives, as well as further objectives that may appear from the description below, are at least partly achieved by a dialysis apparatus, a method of calibrating a dialysis fluid distribution system, a computer-readable medium, and control units according to the independent claims, embodiments thereof being defined by the dependent claims.

A first aspect of the invention is a dialysis apparatus, comprising: a dialyzer; a dialysis fluid distribution system connected for fluid communication with the dialyzer and comprising a first pump and a second pump, the dialysis fluid distribution system being operable to selectively establish a main flow path that extends between the first and second pumps via the dialyzer, and a bypass flow path that bypasses the dialyzer and extends between the first and second pumps; and a control unit electrically connected to the dialysis fluid distribution system and being operable to control a respective frequency of the first and second pumps, wherein the first and second pumps are configured to generate a respective flow rate by repeatedly discharging, at the respective frequency, a respective stroke volume of dialysis fluid. The control unit is configured to, in a calibration mode, operate the dialysis fluid distribution system to establish the bypass flow path, control the first pump to operate at a first calibration frequency and second pump to operate at a second calibration frequency so as to balance the flow rates generated by the first and second pumps, and determine relative calibration data that represents a relation between the stroke volumes of the first and second pumps based on the first and second calibration frequencies. The control unit is further configured to, in a treatment mode, operate the dialysis fluid distribution system to establish the main flow path, and control the first and second pumps, based on said relative calibration data, to operate at a respective treatment frequency so as to generate a selected ultrafiltration rate in the dialyzer.

The first aspect is based on the insight that improved control of the ultrafiltration rate in the dialyzer is enabled if the relation between the stroke volumes of the pumps is known. Thus, the first aspect involves a technique for relatively calibrating the pumps in the dialysis fluid distribution system, in the sense that the relation between the actual stroke volumes of the pumps is determined or estimated. The relative calibration is simple to implement, since it only involves establishing the bypass flow path, and then controlling the first and second pumps to balance the flow rates of dialysis fluid generated by the pumps. The pumps are volumetric pumps, which are configured to generate a respective flow rate by repeatedly discharging, at a respective operating frequency, a respective stroke volume of dialysis fluid. With this type of pump, the relation between the stroke volumes of the pumps may be determined based on the frequency of the respective pump when their flow rates are balanced.

The balancing of the flow rates during the calibration mode may be achieved by the control unit based on the output signal of a relatively simple, robust and inexpensive flow difference meter installed in the dialysis fluid distribution system. The flow difference meter may, e.g., be embodied as a pressure sensor that measures the fluid pressure in the bypass flow path, by a level sensor that measures a level of dialysis fluid in a chamber which is connected in fluid communication with the bypass flow path, or by a flow meter that measures the flow of dialysis fluid to and from such a chamber. It is realized that the exact volume of the chamber is not of importance for the accuracy of the relative calibration of the pumps.

The first aspect also involves a technique of generating a selected ultrafiltration rate in the dialyzer by establishing the main flow path and setting the frequencies of the pumps, based on the relation between the stroke volumes as determined in the relative calibration. In contrast to prior art techniques for controlling ultrafiltration, the first aspect makes it possible to directly and accurately control the difference in flow rates between the pumps during the treatment mode, by setting the frequency of the respective pump. This means that it is possible to dispense with highly advanced, complex and costly flow meters as well as noisy, complex and costly balancing devices. Thereby, the first aspect enables a simplification in the design of the dialysis apparatus. In the absence of balancing chambers and advanced flow meters, the robustness of the dialysis apparatus may also be increased. Further, the dialysis apparatus of the first aspect may be switched to the calibration mode at any time to re-calibrate the relation between the stroke volumes of the pumps. Thus, by the first aspect, the dialysis apparatus may compensate for changes or drifts in the stroke volumes of the pumps. In the absence of a balancing device, the dialysis apparatus may be designed to produce significantly less audible noise.

It should be emphasized, though, that the present invention may be combined with a conventional advanced flow meter for measuring the flow rate of dialysis fluid or a conventional balancing device for balancing the flows of dialysis fluid to and from the dialyzer, if desired.

It should also be noted that the first pump may be located either upstream or downstream of the dialyzer, with the second pump consequently being located either downstream or upstream of the dialyzer. As used herein, "upstream" and "downstream" refers to a direction in relation to the flow of dialysis fluid in the main flow path.

The dialysis apparatus of the first aspect may be operated to control the ultrafiltration in the dialyzer by directly setting the treatment frequencies of the pumps, which are located upstream and downstream of the dialyzer in the main flow path, such that the difference between the flow rates generated by the pumps equals the selected ultrafiltration rate. Alternatively, the dialysis apparatus of the first aspect may be operated to control the ultrafiltration in the dialyzer by setting the treatment frequencies of the pumps such that their flow rates are balanced, and by controlling a dedicated filtration pump, which is connected to the main flow path downstream of the dialyzer, to generate a flow rate equal to the selected ultrafiltration rate.

In one embodiment, the control unit is further configured to, in the calibration mode, store the relative calibration data in an electronic memory for subsequent retrieval by the control unit in the treatment mode.

In one embodiment, the control unit is further configured, in the treatment mode, to assign a predefined nominal stroke volume to the first pump and set the treatment frequency of the first pump so as to generate, based on the predefined nominal stroke volume, a first flow rate of dialysis fluid, and to set the treatment frequency of the second pump, given that the stroke volume of the second pump fulfils said relation with respect to the predefined nominal stroke volume, so as to generate a second flow rate of dialysis fluid which differs from the first flow rate by the selected ultrafiltration rate. The control unit may be configured to set the treatment frequencies of the first and second pumps such that one of the first or second flow rates is equal to a selected flow rate of dialysis fluid out of or into the dialyzer, and the control unit may be further configured to receive a first set value that represents the selected flow rate of dialysis fluid out of or into the dialyzer, and a second set value that represents the selected ultrafiltration rate.

In one embodiment, the control unit, in the treatment mode, is configured to set the treatment frequencies of the first and second pumps (P1, P2) according to:

$$\begin{cases} n1 = \dfrac{Q1}{S1_n} \\ n2 = \dfrac{Q2}{S1_n} \cdot \dfrac{n2_c}{n1_c} \end{cases}$$

wherein n1 is the treatment frequency of the first pump, Q1 is the first flow rate of dialysis fluid generated by the first pump, $S1_n$ is the nominal stroke volume assigned to the first pump, n2 is the treatment frequency of the second pump, Q2 is the second flow rate of dialysis fluid generated by the second pump, $n1_c$ is the first calibration frequency, and $n2_c$ is the second calibration frequency, and wherein the absolute difference between Q1 and Q2 is equal to the selected ultrafiltration rate.

In one embodiment, said relation between the stroke volumes of the first and second pumps is equal to the inverse of the relation between the first and second calibration frequencies.

In one embodiment, the dialysis fluid distribution system further comprises a flow difference meter configured to generate an output signal representative of a difference between the flow rates generated by the first and second pumps, wherein the control unit is operable, in the calibration mode, to balance the flow rates generated by the first and second pumps based on the output signal of the flow difference meter.

In one embodiment, the flow difference meter comprises a pressure sensor arranged to sense a pressure of the dialysis fluid in the dialysis fluid distribution system, and wherein the output signal represents said pressure.

In one embodiment, the bypass flow path is connected in fluid communication with a chamber in the dialysis fluid distribution system, wherein the flow difference meter comprises a level detector, which is arranged to indicate at least one level of dialysis fluid in the chamber, and preferably a range of levels of dialysis fluid in the chamber, and wherein the control unit is operable, in the calibration mode, to balance the flow rates between the first and second pumps by generating a stabilized level of dialysis fluid in the chamber as indicated by the output signal.

In one embodiment, the level detector comprises a pressure sensor which is arranged to sense a pressure in the dialysis fluid distribution system such that an invariant pressure indicates that the level of dialysis fluid is stabilized in the chamber.

In one installation, a top portion of the chamber contains a gas and is sealed during the calibration mode, wherein the pressure sensor is configured to generate the output signal to represent the pressure of the gas in the chamber. The pressure sensor may be installed in contact with the gas to directly measure the gas pressure, or in contact with the dialysis fluid to indirectly measure the gas pressure. In another installation, the pressure sensor is connected to the chamber so as to sense a hydrostatic pressure of the dialysis fluid in the chamber. In the latter installation, a top portion of the chamber may be vented to ambient atmosphere during the calibration mode.

In one implementation, the pressure sensor is arranged to be included in both the bypass flow path and the main flow path. Thereby, the output signal of the pressure sensor may be used by the control unit not only during the calibration mode but also during the treatment mode, e.g. to determine current relative calibration data using a calibration function (below).

In one embodiment, the control unit is configured to, in the calibration mode, operate the first and second pumps to balance the flow rates of dialysis fluid at different working points of the dialysis fluid distribution system; determine the relative calibration data for each of the different working points; and generate a calibration function that relates the relative calibration data to the different working points; and wherein the control unit is configured to, in the treatment mode at a current working point of the dialysis fluid distribution system, obtain current relative calibration data by use of the calibration function and the current working point; and control the first and second pumps, based on the current relative calibration data, to operate at a respective treatment frequency so as to generate a selected ultrafiltration rate in the dialyzer. In one embodiment, the control unit is configured to identify the different working points and the current working point based on an output signal from a pressure sensor arranged to sense a pressure of the dialysis fluid in the dialysis fluid distribution system.

In one embodiment, the control unit is operable to validate the calibration function. In the validation, the control unit is configured to operate the dialysis fluid distribution system to establish the bypass flow path, control the first and second pumps to balance their flow rates at a validation working point of the dialysis fluid distribution system, determine the relative calibration data for the validation working point, and validate the calibration function by comparing the relative calibration data for the validation working point with an output value of the calibration function at the validation working point. The control unit may be configured to take dedicated action based on a difference between the relative calibration data for the validation working point and the output value, said dedicated action comprising at least one of: initiating an alarm, and adjusting the calibration function. The control unit may be configured to adjust the calibration function by adding the difference to the calibration function.

In one embodiment, the control unit is configured to obtain the current relative calibration data by retrieving a current output value of the calibration function at the current working point and compensate the current output value for one or more estimated or measured pressure differences within the dialysis fluid distribution system between the treatment mode and the calibration mode. In one embodiment, the one or more pressure differences relate to at least one of: an inlet of the first pump, an outlet of the first pump, an inlet of the second pump, and an outlet of the second pump. In one general implementation of the dialysis fluid distribution system, the first pump is located upstream of the second pump in the main flow path and the bypass flow path, the treatment frequency of the first pump is invariant during the treatment and calibration modes, and the selected ultrafiltration rate is generated by controlling the treatment frequency of the second pump. In this implementation, the pressure difference between the treatment mode and the calibration mode at the outlet of the second pump may be estimated by the selected ultrafiltration rate, and/or the pressure difference between the treatment mode and the calibration mode at the inlet of the first pump may be estimated to be zero, and/or the pressure difference between the treatment mode and the calibration mode at the inlet of the second pump may be estimated to be zero. The current output value may be further compensated as a function of the flow rate generated by the first pump.

In one embodiment, the control unit is configured to, during the treatment mode, operate a source to generate dialysis fluid by dosing a concentrate into water, said concentrate comprising sodium bicarbonate, and the control unit is configured to, during the calibration mode, disable the dosing of said concentrate into the water.

In one embodiment, the control unit, in the calibration mode, is configured to assign a respective predefined nominal stroke volume to the first and second pumps, operate the first and second pumps at a first and a second start frequency, respectively, such that the first start frequency multiplied by the predefined nominal stroke volume of the first pump is essentially equal to the second start frequency multiplied by the predefined nominal stroke volume of the second pump, and modify at least one of the first and second start frequencies until the flow rates of dialysis fluid generated by the first and second pumps are balanced.

In one embodiment, each of the first and second pumps comprises a respective pulse generator arranged to generate one or more pulses for each stroke volume displaced by the first and second pump, respectively, and wherein the control unit, in the calibration mode, is configured to represent the first and second calibration frequencies by a first number of pulses and a second number of pulses, respectively, generated by the respective pulse generator during a test period while the flow rates of dialysis fluid generated by the first and second pumps are balanced. In an alternative embodiment, the control unit is configured to represent the first and second calibration frequencies by a respective set value for the first and second pumps while the flow rates of dialysis fluid generated by the first and second pumps are balanced.

In one embodiment, the first pump is located upstream of the dialyzer in the main flow path and the second pump is located downstream of the dialyzer in the main flow path.

In one embodiment, each of the first and second pumps is one of a diaphragm pump and a piston pump.

A second aspect of the invention is a method of operating a dialysis fluid distribution system that comprises first and second pumps which are connected for fluid communication on a main flow path that extends between first and second pumps via a dialyzer, wherein the first and second pumps are configured to generate a respective flow rate by repeatedly discharging, at a respective frequency, a respective stroke volume of the dialysis fluid. The method comprises a calibration procedure and a treatment procedure. The calibration procedure comprises: operating the dialysis fluid distribution system to establish a bypass flow path, which bypasses the dialyzer and extends between the first and second pumps, controlling the first pump to operate at a first calibration frequency and the second pump to operate at a second calibration frequency so as to balance the flow rates generated by the first and second pumps, and determining, based on the first and second calibration frequencies, relative calibration data that represents a relation between the stroke volumes of the first and second pumps. The treatment procedure comprises: operating the dialysis fluid distribution system to establish the main flow path, and controlling the first and second pumps, based on said relative calibration data, to operate at a respective treatment frequency so as to generate a selected ultrafiltration rate in the dialyzer.

A third aspect of the invention is a computer-readable medium comprising program instructions which, when executed by a processing unit, is adapted to carry out the method of the second aspect.

Fourth and fifth aspects of the invention concern a control unit for a dialysis fluid distribution system arranged in a dialysis apparatus to pump a dialysis fluid through a dialyzer. The dialysis fluid distribution system comprises first and second pumps which are connected for fluid communication on a main flow path that extends between the first and second pumps via the dialyzer, wherein the first and second pumps are configured to generate a respective flow rate by repeatedly discharging, at a respective frequency, a respective stroke volume of the dialysis fluid.

The control unit of the fourth aspect comprises: a signal communication interface for connection to the dialysis fluid distribution system; and a signal processor operable in a calibration mode and a treatment mode, wherein the signal processor, in the calibration mode and via the signal communication interface, is configured to: operate the dialysis fluid distribution system to establish a bypass flow path, which bypasses the dialyzer and extends between the first and second pumps; control the first pump to operate at a first calibration frequency and the second pump to operate at a second calibration frequency so as to balance the flow rates generated by the first and second pumps; and determine, based on the first and second calibration frequencies, relative calibration data that represents a relation between the stroke volumes of the first and second pumps; and wherein the signal processor, in the treatment mode and via the signal communication interface, is configured to: operate the dialysis fluid distribution system to establish the main flow path; and control the first and second pumps, based on said relative calibration data, to operate at a respective treatment frequency so as to generate a selected ultrafiltration rate in the dialyzer.

The control unit of the fifth aspect comprises: means for operating the dialysis fluid distribution system to establish a bypass flow path, which bypasses the dialyzer and extends between the first and second pumps; means for controlling the first pump to operate at a first calibration frequency and the second pump to operate at a second calibration frequency so as to balance the flow rates generated by the first and second pumps; means for determining, based on the first and second calibration frequencies, relative calibration data that represents a relation between the stroke volumes of the first and second pumps; means for operating the dialysis fluid distribution system to establish the main flow path; and means for controlling the first and second pumps, based on said relative calibration data, to operate at a respective treatment frequency so as to generate a selected ultrafiltration rate in the dialyzer.

Any one of the above-identified embodiments of the first aspect may be adapted and implemented as an embodiment of the second to fifth aspects.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings. Throughout the description, the same reference numerals are used to identify corresponding elements.

DETAILED DESCRIPTION OF EXAMPLE EMBODIMENTS

Figure 1:
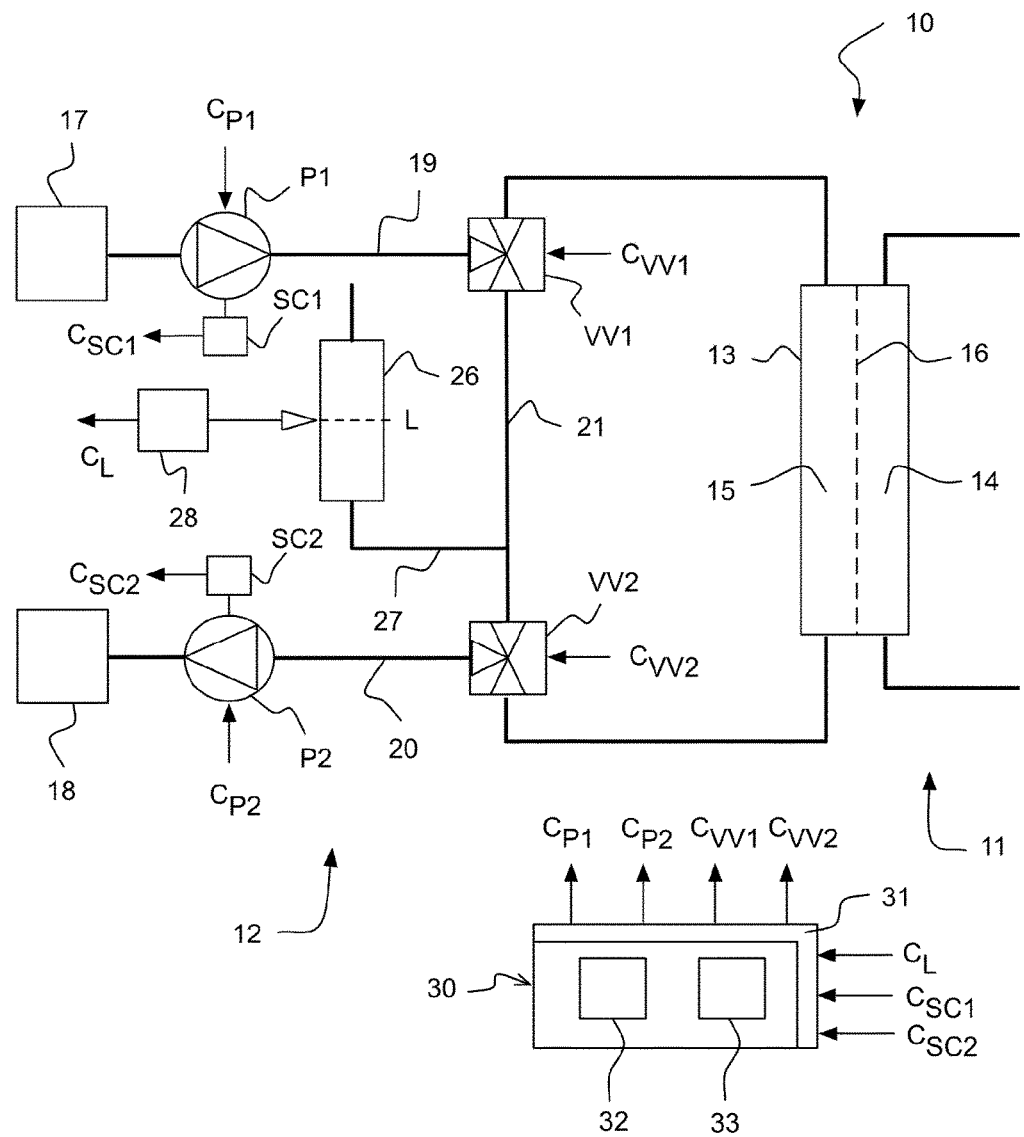
FIG. 1 is a block diagram of a system for ultrafiltration according to an embodiment.

FIG. 1 illustrates an embodiment of a system 10 for ultrafiltration. The system 10 may be included in a dialysis apparatus. It is understood that only components relevant to the following description are represented in FIG. 1, with other components being well within the purview of one skilled in the art to ascertain. The system 10 comprises a blood circuit 11, a dialysis fluid circuit 12 and a dialyzer 13. The dialyzer 13 is a blood filtration unit that generally has a blood side 14 and a dialysis fluid side 15 separated by a semipermeable membrane 16. The blood circuit 11 is connected to an inlet and an outlet of the blood side 14. One or more pumps (not shown) are arranged in the blood circuit 11 to pump blood from a source (not shown) through the dialyzer 13 to a receptacle (not shown). The blood may e.g. be pumped from the cardiovascular system of a subject and back to the subject, as is well-known in the art. The dialyzer 13 may be any of the well-known dialyzers useful for hemodialysis, such as a coil dialyzer, a parallel plate dialyzer, a hollow fiber dialyzer, etc.

The dialysis fluid circuit 12 extends from a source 17 of fresh dialysis fluid to a receptacle or drain 18 for spent dialysis fluid. The dialysis fluid circuit 12 includes an arrangement of fluid lines that define an inlet conduit 19 connected to an inlet of the dialysis fluid side 15 of the dialyzer 13, an outlet conduit 20 connected to an outlet of the dialysis fluid side 15 of the dialyzer 13, and a bypass conduit 21 that extends between the inlet and outlet conduits 19, 20. A first pump P1 ("upstream pump") is arranged in the inlet conduit 19 to pump dialysis fluid from the source 17, and a second pump P2 ("downstream pump") is arranged in the outlet conduit 20 to pump dialysis fluid towards the receptacle 18. A first and a second three-way valve VV1, VV2 are arranged in the inlet conduit 19 and the outlet conduit 20, respectively, and are connected to the bypass conduit 21. The first valve VV1 is operable to establish fluid communication either between the first pump P1 and the dialyzer 13, or between the first pump P1 and the bypass conduit 21. The second valve VV2 is operable to establish fluid communication either between the dialyzer and the second pump P2, or between the bypass conduit 21 and the second pump P2. A chamber 26, denoted calibration chamber in the following, is arranged in fluid communication with the bypass conduit 21 via a connecting conduit 27. A level detector 28 is installed to generate a sensor signal $C_L$ which is indicative of at least one fluid level L in the calibration chamber 26. The level detector 28 may be of any conventional type that allows single-point, multi-point or continuous level detection, such as an ultrasonic detector, an optical detector, a capacitive detector, a microwave sensor, a hydrostatic sensor, a magnetic float detector, etc. In a specific embodiment, described below with reference to FIG. 7, continuous level detection is achieved by pressure detection in the calibration chamber 26.

The pumps P1, P2 are "volumetric pumps", which means that each pump is configured to generate a given flow rate by repeatedly discharging a respective stroke volume of dialysis fluid. Volumetric pumps are well-known per se and are also referred to as positive displacement pumps. A volumetric pump is configured to drive a fluid by trapping a fixed and well-defined volume of the fluid in a pump chamber and by forcing (displacing) that trapped volume through a pump outlet by a movable pumping element, e.g. a piston or a diaphragm. Volumetric pumps that may be used in the embodiment of FIG. 1 include reciprocating pumps such as piston pumps and diaphragm pumps. One characteristic of volumetric pumps is that they have a well-defined stroke volume, and that the flow rate of a volumetric pump is controlled via the frequency of the pump, i.e. the frequency of the stroke volumes that are discharged by the pump. In the following, the "speed" of a pump is synonymous with the frequency of stroke volumes.

Each pump P1, P2 is equipped or associated with a respective pulse generator SC1, SC2 that generates one or more pulses for each stroke volume that is displaced by the pump P1, P2. Such pulse generators are well-known in the art and may e.g. be implemented as a pulse encoder or a tachometer. Each pulse may correspond to a predefined displacement of above-mentioned pumping element. As indicated in FIG. 1, the pulse generators SC1, SC2 are configured to generate a respective pulse signal $C_{SC1}$, $C_{SC2}$ that is indicative of the pulses that are generated during operation of the pumps P1, P2. The pulse signals $C_{SC1}$, $C_{SC2}$ may be used by the control unit 30 (below), or a dedicated pump controller (not shown), for feedback control of the speed of the respective pump P1, P2 in a manner well-known in the art. In certain embodiments, as will be further described below, the pulse signals $C_{SC1}$, $C_{SC2}$ are also used by the control unit 30 for relatively calibrating the stroke volumes of the first and second pumps P1, P2.

As indicated, the system 10 further includes an electronic control unit 30. The control unit 30 has a signal communication interface 31 for electrical connection to electrically responsive components in the dialysis fluid circuit 12. Specifically, the control unit 30 is operable to receive the sensor signal $C_L$ from the level detector 28 and the pulse signals $C_{SC1}$, $C_{SC2}$ from the pulse generators SC1, SC2. The control unit 30 is further operable to generate and output control signals $C_{P1}$, $C_{P2}$ for controlling the operation of the pumps P1, P2 and control signals $C_{VV1}$, $C_{VV2}$ for controlling the switching of the valves VV1, VV2. The control unit 30 may implement further functions of the dialysis apparatus and may be included as a part of a control system for the dialysis apparatus. The control unit 30 may be a computer, or a similar data processing device, with adequate hardware for acquiring, processing and generating signals in accordance with different embodiments of the invention. Embodiments of the invention may be implemented by software instructions that are supplied on a computer-readable medium for execution by a processor 32 in conjunction with an electronic memory 33 in the device 30, as indicated in FIG. 1. The computer-readable medium may be a tangible product (e.g. magnetic medium, optical disk, read-only memory, flash memory, etc) or a propagating signal.

The system 10 is operable in a treatment mode or procedure, in which the control unit 30 controls the dialysis fluid circuit 12 to generate a flow of dialysis fluid through the dialysis fluid side 15 of the dialyzer 13. During the treatment mode, the pumps P1, P2 are set to generate different flow rates, such that the flow rate of the downstream pump P2 exceeds the flow rate of the upstream pump P1 by the desired ultrafiltration rate in the dialyzer 13. As explained in the Background section, the ultrafiltration rate (or UF rate) is the rate of fluid removal from the blood that takes place in the dialyzer 13. In blood treatment, ultrafiltration generally denotes a process of removing water from blood plasma. The blood is passed on the blood side 14 of the dialyzer 13, and a gradient of pressure is created through the semipermeable membrane 16 by the difference in flow rates between the pumps P1, P2. The pressure gradient forces fluid through the pores of the membrane 16. The pores filter electrolytes and small and middle sized molecules (up to 20,000 to 30,000 daltons) from the blood plasma.

The volumetric pumps P1, P2 are manufactured with a nominal stroke volume. However, the actual stroke volume of an individual pump may differ from the nominal stroke volume due to tolerances in manufacture and assembly of the pump. Further, the stroke volume may change during operation of the pump, e.g. due to build-up of deposits or contaminations in the pump chamber or due to wear of the pumping element or the pump chamber. Depending on the type of pump, the stroke volume may also vary depending on the fluid pressure at the inlet and/or outlet of the pump.

Even small differences between the actual and nominal stroke volumes of the pumps P1, P2 may lead to a large deviation between the desired UF rate and the actual UF rate that is generated by the flow rate difference between the pumps P1, P2. This sensitivity will be illustrated by reference to a numeric example. Assume that the pumps P1, P2 are identical to the degree that their nominal stroke volume is 3.8 ml but that their actual stroke volumes deviate by −1% and +1%, respectively, from the nominal stroke volume. Also assume that the set value for the inlet flow of dialysis fluid to the dialyzer is 500 ml/min and that the desired UF rate is 500 ml/h. Using the nominal stroke volumes to achieve this UF rate, the speed of pump P1 is set to 500/3.8=131.58 strokes/min and the speed of pump P2 is set to (500+500/60)/3.8=133.77 strokes/min. However, based on the actual stroke volumes, the pump P1 will generate a flow rate of 131.58*3.8*1.01=505.00 ml/min and pump P2 will generate a flow rate of 133.77*3.8*0.99=503.25 ml/min. Thus, the actual UF rate is (503.25−505.00)*60=−105 ml/h. This means that instead of removing 500 ml fluid per hour from the blood, the system will pump 105 ml fluid per hour into the blood.

It is realized that proper control of the UF rate may require the pumps P1, P2 to be manufactured with very tight tolerances so that the actual stroke volumes closely correspond to the nominal stroke volumes. To overcome this drawback, embodiments of the invention take the approach of relatively calibrating the pumps P1, P2 before or even during ongoing blood processing. To this end, the system 10 is configured to be operable in a calibration mode or procedure, in which a relation between the actual stroke volumes of the pumps P1, P2 is determined by clever control of the pumps P1, P2 and use of the calibration chamber 26. The calibration mode is implemented by the control unit 30, which generates dedicated control signals $C_{P1}$, $C_{P2}$, $C_{VV1}$, $C_{VV2}$ based on the sensor signal $C_L$, and processes the pulse signals $C_{SC1}$, $C_{SC2}$ for determination of the relation between the actual stroke volumes. In the following, the actual stroke volumes of the pumps P1, P2 are represented as S1, S2, respectively, and the nominal stroke volumes of the pumps P1, P2 are represented as $S1_n$, $S2_n$, respectively.

An embodiment of the calibration mode 100 is represented in the flow chart of FIG. 2 and will be discussed below with further reference to FIG. 3. In a first step 101, the valves VV1, VV2 are controlled to establish a direct flow path between the pumps P1, P2, i.e. a flow path that bypasses the dialyzer 12. This bypass flow path is also in fluid communication with the calibration chamber 26. In the example of FIG. 3, the valves VV1, VV2 are controlled to establish fluid communication between the inlet and outlet conduits 19, 20 via the bypass conduit 21, while closing off the fluid communication to and from the dialyzer 13. Thereby, all of the fresh dialysis fluid will be pumped from the source 17 through the bypass conduit 21 to the receptacle 18. In FIG. 3, a closed valve passage is represented by a filled triangle and an open valve passage is represented by an open triangle. In step 102, the pumps P1, P2 are controlled to generate a stable level of dialysis fluid in the calibration chamber 26, as indicated by the sensor signal $C_L$. This means that the flow rates of the pumps P1, P2 are balanced, i.e. the flow rate generated by pump P1 is essentially identical to the flow rate generated by pump P2. Even if it is possible to balance the flow rates using a level detector 28 indicating a single predefined level L in the chamber 26, the balancing is generally facilitated if the level detector 28 is arranged for multi-point or continuous level measurements. In one non-limiting example, the pumps P1, P2 are first set to operate at start frequencies that are known to nominally generate the same reference flow rate, given the nominal stroke volumes $S1_n$, $S2_n$ of the pumps P1, P2. The reference flow rate or the start frequencies may be predefined and retrieved from memory 33 in step 102. The frequency of one or both of the pumps P1, P2 is then adjusted until the fluid level in the chamber 26 is stabilized. It should be noted that the absolute location of the fluid level in the chamber 26 is not important. The skilled person realizes that there are many alternative ways of controlling the pumps P1, P2 based on the level signal $C_L$ to stabilize the fluid level in the chamber 26.

In step 103, while the pumps are operated to generate a stabilized fluid level in the chamber 26, the current speed of the respective pump P1, P2 is determined. In the following, the current speeds are also denoted "calibration frequencies" and are represented as $n1_c$, $n2_c$. In one embodiment, the control unit 30 determines the current speeds $n1_c$, $n2_c$ based on the current set values for the pumps P1, P2. In an alternative embodiment, to increase accuracy, the control unit 30 counts the number of pulses in the pulse signals $C_{SC1}$, $C_{SC2}$ during a predefined time period, which may but need not be the same for both pumps P1, P2. The current speeds $n1_c$, $n2_c$ may be represented by the respective count of pulses or by a frequency value which is generated based on the count of pulses (e.g. by dividing the count of pulses by the respective time period).

In step 104, the pumps P1, P2 are relatively calibrated, by calculating a ratio R between their actual stroke volumes S1, S2. The rationale behind this operation is that that balanced flows for volumetric pumps are given by:

$$n1_c \cdot S1 = n2_c \cdot S2 \quad (1)$$

and thus the stroke volume ratio R is given by:

$$R = \frac{S1}{S2} = \frac{n2_c}{n1_c} \quad (2)$$

In step 105, the stroke volume ratio R is stored in the electronic memory (33 in FIG. 1) for subsequent retrieval when the system 10 enters a treatment mode (see below).

Figure 5:
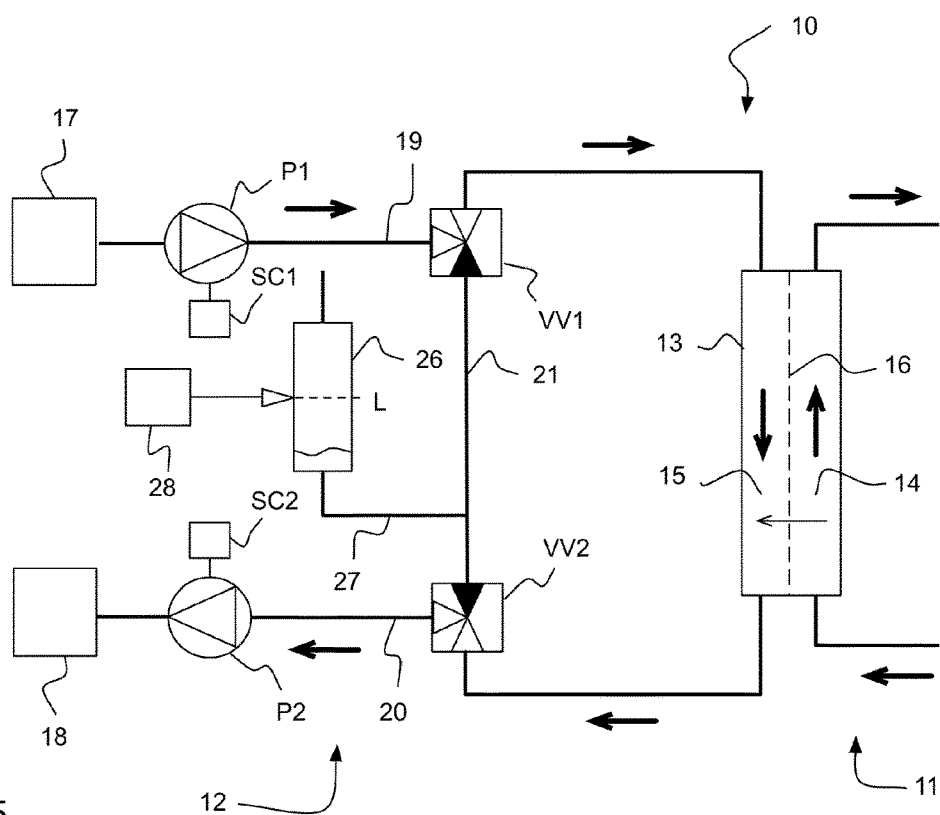
FIG. 5 illustrate the operation of the system in FIG. 1 during the treatment mode in FIG. 4.

As noted, the system 10 in FIG. 1 is also operable in a treatment mode, in which a desired UF rate is achieved in the dialyzer 13. An embodiment of the treatment mode 200 is represented in the flow chart of FIG. 4 and will be discussed below with further reference to FIG. 5. In a first step 201, the valves VV1, VV2 are controlled to establish a flow path ("main flow path") from the pump P1 via the dialysis fluid side 15 of the dialyzer 13 to the pump P2, such that all of the fresh dialysis fluid from source 17 is pumped through the dialyzer 13 and that all of the spent dialysis fluid is pumped from the dialyzer 13 to the receptacle 18. In the example of FIG. 5, the valves VV1, VV2 are controlled to establish fluid communication between the inlet and outlet conduits 19, 20 and the dialyzer 13, while closing off the fluid communication between the inlet and outlet conduits 19, 20 and the bypass conduit 21. In step 202, set values are obtained for the flow rate of dialysis fluid into the dialyzer 13, denoted main flow rate and designated by $Q_{MAIN}$, and the ultrafiltration rate, designated by $Q_{UF}$. The set values $Q_{MAIN}$, $Q_{UF}$ may be pre-stored in and retrieved from the memory 33 or they may be acquired in real time via a user interface (not shown) associated with the control unit 30 or the dialysis apparatus. In step 203, the stroke volume ratio R that was determined by the control unit 30 in the calibration mode (FIG. 2) is retrieved, e.g. from the memory 33 or via the above-mentioned user interface. In step 204, the nominal stroke volume $S1_n$ of the upstream pump P1 is retrieved from memory 33. In step 205, the speed n1 of the upstream pump P1 is calculated and set to generate a flow rate Q1 which is equal to the main dialysis flow $Q_{MAIN}$, given the nominal stroke volume $S1_n$, i.e.

$$n1 = \frac{Q1}{S1_n} = \frac{Q_{MAIN}}{S1_n} \quad (3)$$

Thus, step 205 assumes that the actual stroke volume Si is equal to the nominal stroke volume $S1_n$. As will be shown below, even if this assumption is generally incorrect and introduces an error in the flow of dialysis fluid generated by pump P1, the impact of this error on the UF rate is limited by proper use of the stroke volume ratio R when setting the speed of the downstream pump P2. In step 206, the speed n2 of the downstream pump P2 is calculated and set to achieve a difference of flow rates between the pumps P1, P2 equal to the ultrafiltration rate $Q_{UF}$, given by the relation between the actual stroke volumes S1, S2 obtained in the calibration mode 100 and represented by the stroke volume ratio R. Specifically, the downstream pump P2 should be set to generate a flow rate Q2 which is equal to $Q_{MAIN}+Q_{UF}$. Given the assumption that the actual stroke volume of the upstream pump P1 is $S1_n$, the actual stroke volume S2 of the downstream pump P2 is estimated as:

$$S2_{est} = \frac{S1_n}{R} \quad (4)$$

Based on the estimated stroke volume $S2_{est}$, the speed n2 of the downstream pump P2 is set to:

$$n2 = \frac{Q_2}{S2_{est}} = \frac{Q_{MAIN} + Q_{UF}}{S2_{est}} = \frac{Q_{MAIN} + Q_{UF}}{S1_n} \cdot R \quad (5)$$

Following step 206 and as indicated by thick arrows in FIG. 5, dialysis fluid will now be pumped through the dialysis fluid side 15 of the dialyzer 13, while blood is being pumped through the blood side 14 of the dialyzer 13. The difference in flow rates between the pumps P1, P2 draws ultrafiltrate from the blood into the dialysis fluid, as indicated by the horizontal arrow in the dialyzer 13 in FIG. 5.

It is to be understood that the set value $Q_{UF}$ may vary during a treatment, and the control unit 30 will control the speed n2 of the downstream pump P2 accordingly. The set value $Q_{MAIN}$ is typically held constant during a treatment, although it can certainly be varied if desired.

The accuracy of the resulting UF rate is dependent on the accuracy of the stroke volume ratio R, which in turn is dependent on the accuracy of the calibration frequencies $n1_c$, $n2_c$ that are determined in step 103 in the calibration mode 100. It should be noted that the relative calibration of the pumps is independent of the volume of the calibration chamber 26. As noted above, a deliberate error is introduced in step 205 when the actual stroke volume of one of the pumps P1, P2 is set equal to the nominal stroke volume. However, this error has limited impact on the resulting UF rate as will be shown in the following. The actual stroke volumes are represented as $S1=S1_n*e1$ and $S2=S2_n*e2$, where e1, e2 are relative errors caused by the difference between the actual and nominal stroke volumes. The actual UF rate $Q_{UF\_real}$ is given by, using Eq. (5) and Eq. (3):

$$Q_{UF\_real} = S2 \cdot n2 - S1 \cdot n1 \quad (6)$$

$$= S2_n \cdot e2 \cdot \frac{Q_{MAIN} + Q_{UF}}{S1_n} \cdot R - Q_{MAIN} \cdot e1$$

Further, since $$R = \frac{S1}{S2} = \frac{S1_n \cdot e1}{S2_n \cdot e2} \quad (7)$$

it is possible to re-write Eq. (6) as:

$$Q_{UF\_real} = e1 \cdot (Q_{MAIN} + Q_{UF}) - Q_{MAIN} \cdot e1 = Q_{UF} \cdot e1 \quad (8)$$

As seen, the resulting error in the actual UF rate is proportional to the relative difference or error between the actual and nominal stroke volumes for the upstream pump P1, which is assumed to have an actual stroke volume equal to the nominal stroke volume. Reverting to the numeric example given above, where the actual stroke volumes of the pumps P1, P2 in FIG. 1 deviate by −1% and +1%, respectively, from the nominal stroke volume and the desired UF rate is 500 ml/h, the actual UF rate is 500*0.99=495 ml/h, which is significantly better that the actual UF rate of −105 ml/h that is attained without the inventive calibration. It should be noted that the stroke volume error of 1% is merely given as an example and that significantly larger stroke volume errors may be accepted.

Figure 4:
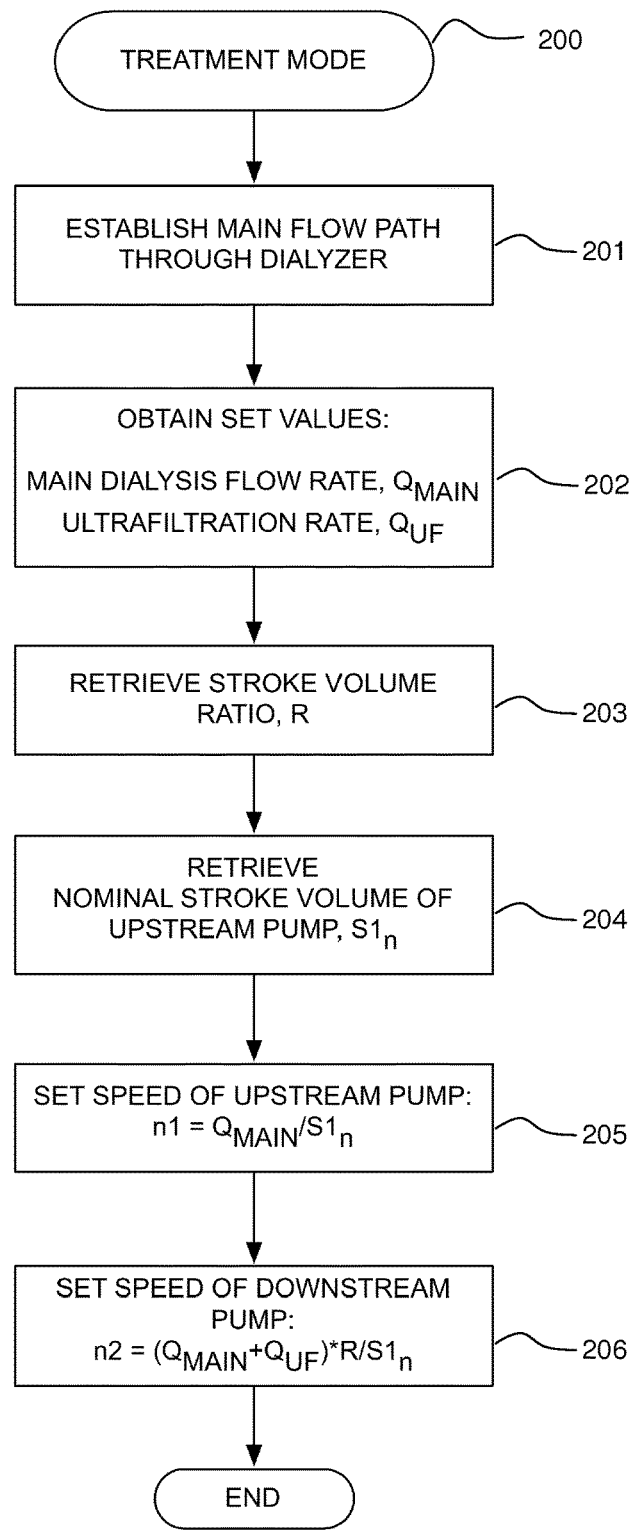
FIG. 4 is a flow chart of a treatment mode executed by the control unit in the system of FIG. 1.

It should be understood that FIG. 4 is an example embodiment and that many alternatives and variants are conceivable. For example, the method may be modified to assume that the actual stroke volume of the downstream pump P2 (instead of the upstream pump P1) is equal to the nominal stroke volume. In such an alternative, step 204 may be modified to retrieve the nominal stroke volume $S2_n$ of the downstream pump P2, and steps 205-206 may be modified to calculate the speeds according to: $n1=Q_{MAIN}/(R*S2_n)$ and $n2=(Q_{MAIN}+Q_{UF})/S2_n$.

In a further variant, the set value $Q_{MAIN}$ instead represents the flow of dialysis fluid out of the dialyzer 13. The skilled person can readily adapt steps 205-206 to this situation. In many dialysis systems, it is desirable to maintain a constant flow of dialysis fluid from the source 17, e.g. when the source 17 is configured to prepare the dialysis fluid by mixing of one or more concentrates with water. The complexity of such a source 17 may increase if the source 17 need to handle momentary changes in the amount of dialysis fluid to be output. In such dialysis systems, the embodiment in FIG. 5 may be preferable, where the UF rate is controlled by adjusting the speed of the downstream pump P2.

Figure 2:
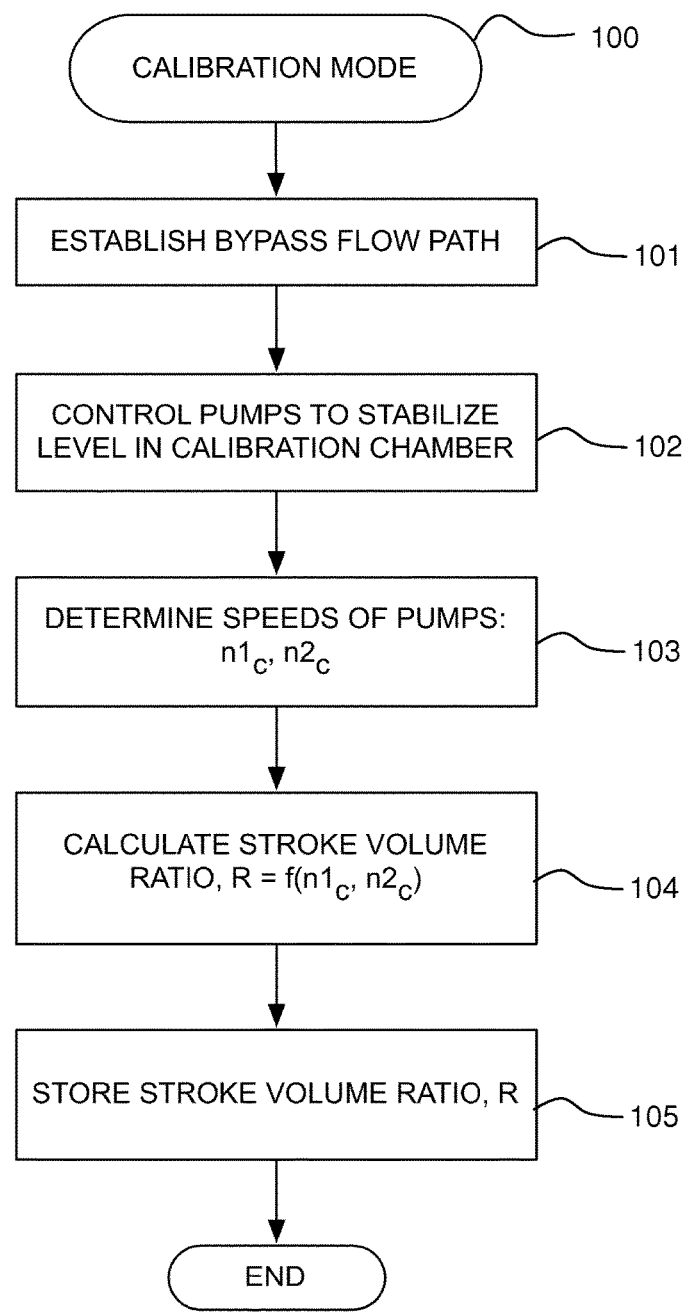
FIG. 2 is a flow chart of a calibration mode executed by a control unit in the system of FIG. 1.
Figure 3:
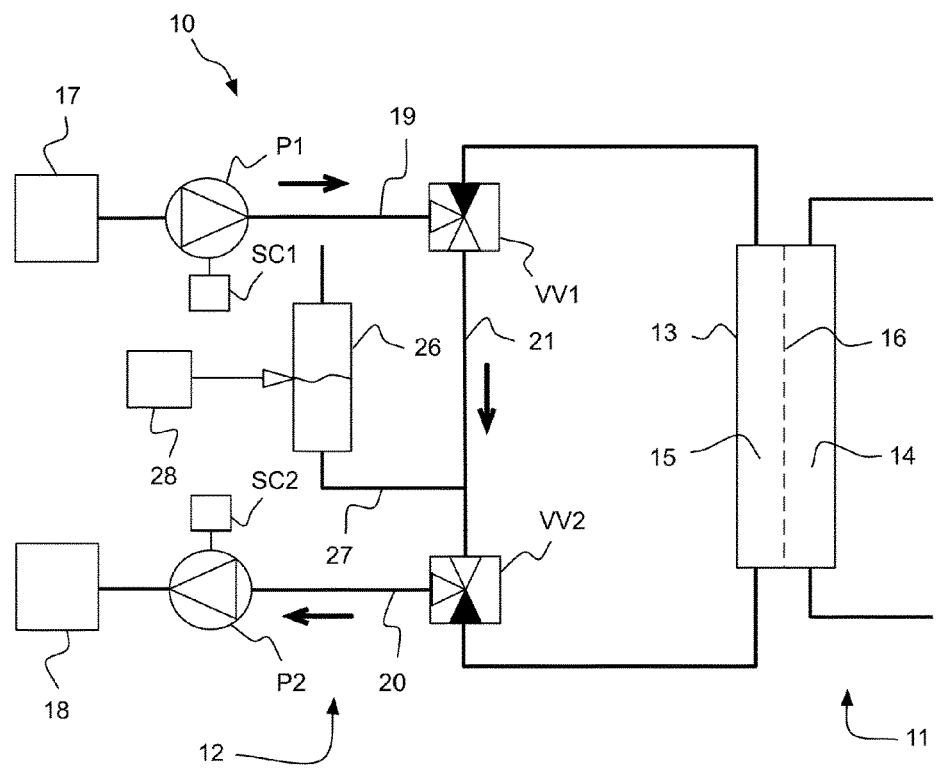
FIG. 3 illustrate the operation of the system in FIG. 1 during the calibration mode in FIG. 2.

Reverting to the calibration mode 100 in FIG. 2, it should be understood that the stroke volume ratio $R=n2_c/n1_c$ is only one of many possible representations of the relation between the actual stroke volumes of the pumps P1, P2. Generally, step 104 may be seen to generate "relative calibration data", which represents the relation between the actual stroke volumes. The relative calibration data may alternatively be given by the ratio $n1_c/n2_c$ or by the speed values $n1_c$ and $n2_c$ that are determined in step 103.

It is also conceivable that the control unit 30, when in calibration mode 100, executes steps 102-103 to determine relative calibration data, e.g. stroke volume ratios R, for a number of different working points of the dialysis fluid circuit 12, and that the control unit 30 in step 104 stores a calibration function in the electronic memory 33, where the calibration function may be implemented as individual combinations of relative calibration data and the different working points, or as a mathematical function that represents the functional relationship between the relative calibration data and the different working points. Such a variant may be desirable if the actual stroke volumes are known to vary during operation of the dialysis fluid circuit 12. For example, the actual stroke volumes may vary if there is a leakage flow of dialysis fluid past the pumping element in the respective pump P1, P2 (e.g. a backflow from the outlet to the inlet of the respective pump, or a reverse backflow from the inlet to the outlet) and if this leakage flow changes with operating condition. The leakage flow may e.g. vary with the fluid pressure at the inlet and/or outlet of the respective pump. To counteract such variations in the actual stroke volumes, the control unit 30 may in step 203 retrieve from the memory 33 the relative calibration data (e.g. stroke volume ratio R) for the working point that comes closest to the current working point of the dialysis fluid circuit 12, or by inputting the current working point to the above-mentioned mathematical function. The working point may be represented by any combination of set values and/or measurement data, such as the set value $Q_{MAIN}$ or one or more measured pressure values that represent the fluid pressure at the inlet/outlet of one or both pumps P1, P2. In one example, a pressure differential between the inlet and the outlet of the respective pump P1, P2 is measured and used to represent the working point of the dialysis fluid circuit 12. In another example, which is further described below with reference to FIG. 10, the working point is represented by the measured pressure of the dialysis fluid in the dialysis fluid circuit 12.

It is to be understood that the control unit 30 may be operated in the calibration mode at any time, e.g. at manufacture of a dialysis machine that includes the dialysis fluid circuit, at scheduled maintenance, before start of a dialysis treatment, intermittently during a dialysis treatment, or after a completed dialysis treatment. Each calibration mode results in relative calibration data that quantifies the relation between the actual stroke volumes S1, S2 of the pumps P1, P2.

Figure 6:
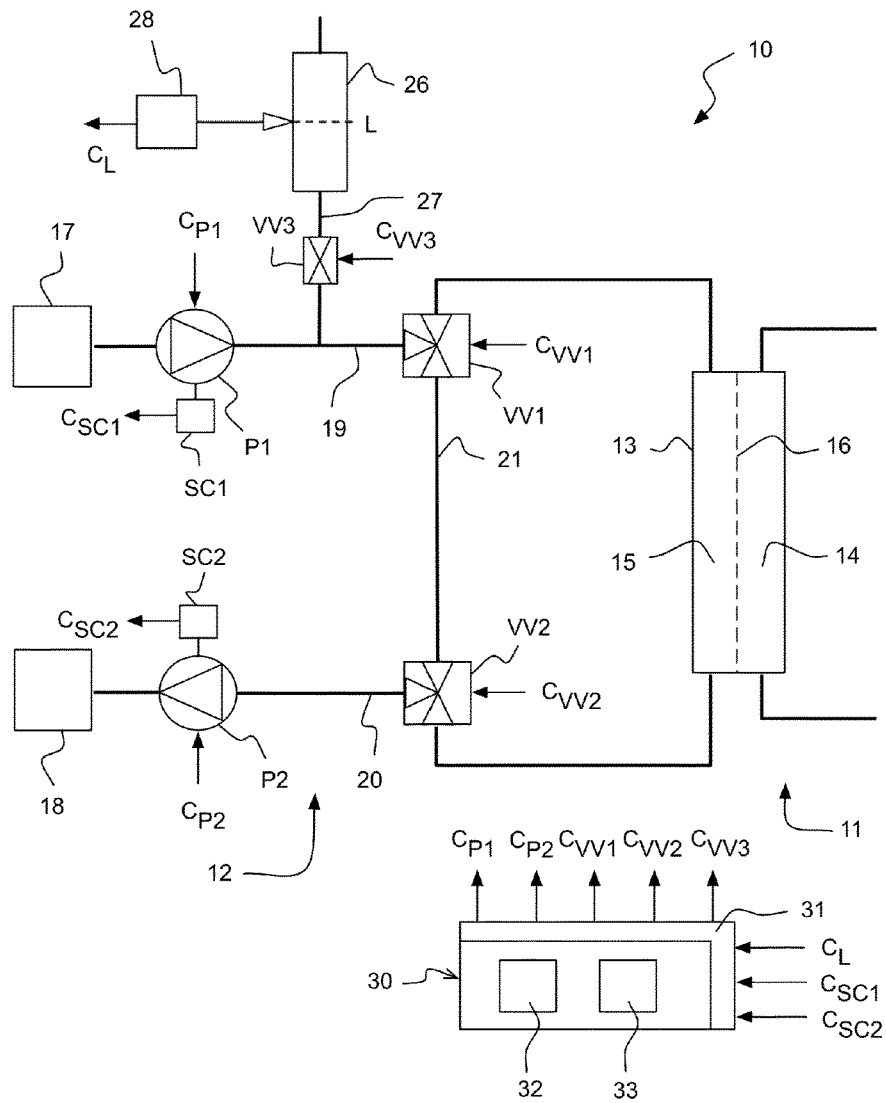
FIG. 6 is a block diagram of a system for ultrafiltration according to another embodiment.

FIG. 6 illustrates another embodiment of a system 10 for ultrafiltration. The system 10 in FIG. 6 differs from the system in FIG. 1 by the placement of the calibration chamber 26. The chamber 26 is arranged for fluid communication with the inlet conduit 19 between the upstream pump P1 and the first valve VV1 via a connecting conduit 27. An on/off valve VV3 is arranged in the connecting circuit 27 to selectively establish fluid communication between the chamber 26 and the inlet conduit 19. The control unit 30 is configured to generate a control signal $C_{VV3}$ for controlling the opening and closing of the valve VV3. The foregoing embodiments, variants and examples are equally applicable to the embodiment in FIG. 6, with the difference that the control unit 30 operates the valve VV3 to open the connecting conduit 27 when the bypass flow path is established in step 101 during the calibration mode 100, and operates the valve VV3 to close off the connecting conduit 27 when the main flow path is established in step 201 during the treatment mode 200. In variant (not shown), the chamber 26 is instead connected for fluid communication with the outlet conduit 20 between the second valve VV2 and the pump P2.

Figure 7:
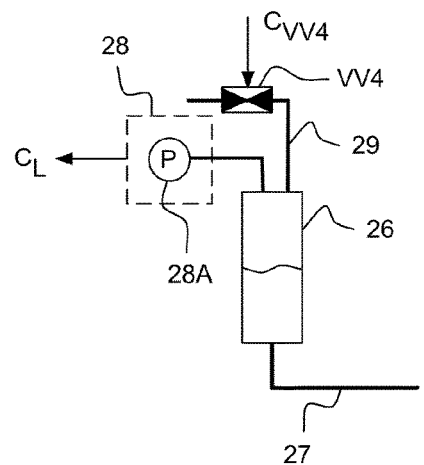
FIG. 7 is an elevated side view of a calibration chamber associated with a pressure-based level detector.

FIG. 7 shows an embodiment of a level detector 28 that operates by sensing the pressure in the calibration chamber 26. Such a level detector 28 is capable of generating a sensor signal $C_L$ that represents a continuous range of fluid levels in the chamber 26. The level detector 28 includes a pressure sensor 28A which is installed to sense the gas pressure above the dialysis fluid in the chamber 26. In the illustrated example, the top of the chamber 26 is vented via an outlet conduit 29, and an on/off valve VV4 is arranged in the outlet conduit 29. The control unit 30 is arranged to generate a control signal $C_{VV4}$ to control the opening and closing of the valve VV4. During level sensing, e.g. in the calibration mode 100, the control unit 30 closes valve VV4 to confine a gas (air) in the space above the dialysis fluid. Thereby, the gas pressure will vary with the volume of the space above the dialysis fluid according to Boyle's law. Thus, changes in measured gas pressure, as represented in the sensor signal $C_L$, corresponds to changes in fluid level. In a variant, the outlet conduit 29 is omitted and the chamber 26 is permanently sealed.

In an alternative embodiment (not shown), the pressure sensor 28A is instead installed at the bottom of the calibration chamber 26 to sense the hydrostatic pressure of the dialysis fluid. As is well-known, the hydrostatic pressure varies in proportion to the fluid level because of the increasing weight of dialysis fluid exerting downward force from above. To reduce the impact of changes in gas pressure in the space above the dialysis fluid, the valve VV4 may be controlled to open during the level sensing. In a variant, the valve VV4 is omitted and the chamber 26 is open to ambient atmosphere.

Figure 8:
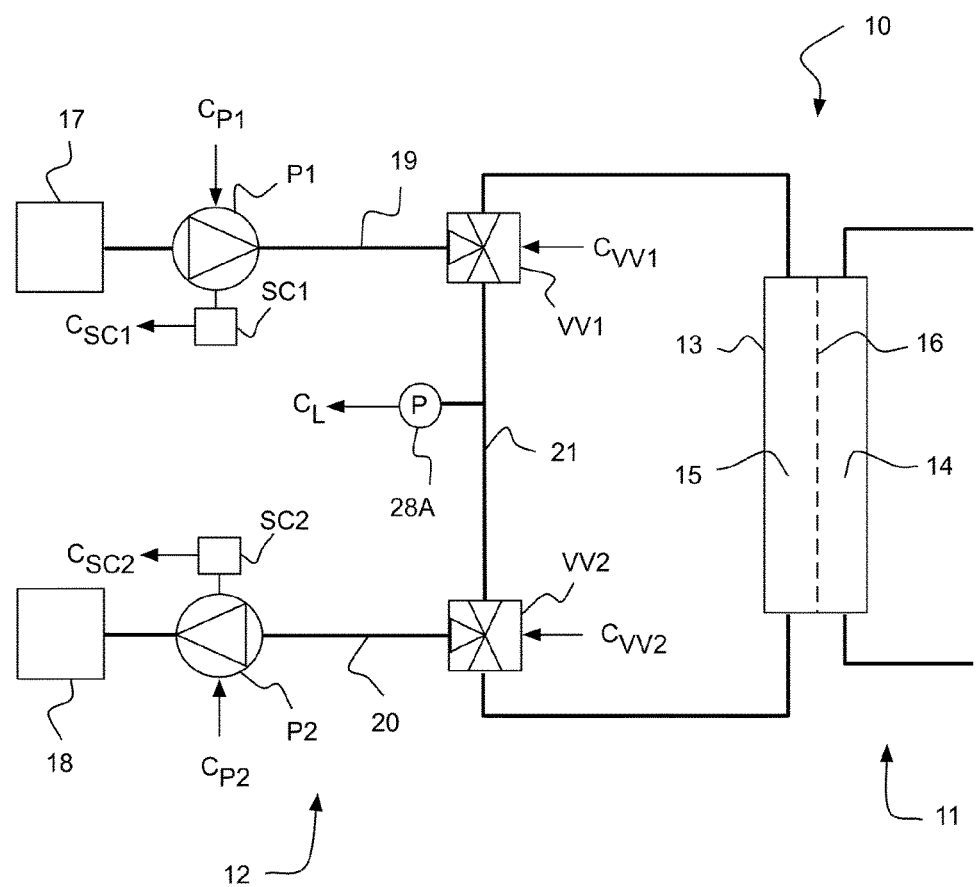
FIGS. 8-9 are block diagrams of systems for ultrafiltration according to further embodiments.

FIG. 8 illustrates yet another embodiment of a system 10 for ultrafiltration. The system 10 in FIG. 8 is identical to the system in FIG. 1 except for the equipment used for balancing the flow rates of the pumps P1, P2 during the calibration mode. In FIG. 8, the chamber 26 and the level detector 28 are replaced by a pressure sensor 28A, which is installed to generate a sensor signal $C_L$ that represents the pressure of the dialysis fluid in the bypass conduit 21. It is realized that the pressure sensor 28A generates a time-invariant pressure value when the flow rates of the pumps P1, P2 are balanced. Thus, the system in FIG. 8 may be operated according to the flow chart in FIG. 2, with the difference that step 102 involves controlling the pumps P1, P2 to stabilize the pressure as measured by the pressure sensor 28A. In a variant (not shown), the pressure sensor 28A is instead installed in the inlet conduit 19 between the pump P1 and the first valve VV1, or in the outlet conduit 20 between the second valve VV2 and the pump P2.

Since the dialysis fluid is an incompressible fluid, comparatively small differences between the flow rates of the pumps P1, P2 during the calibration mode may give rise to large pressures in the dialysis fluid. Excessive pressures in the dialysis fluid may cause leaks or damage the pumps P1, P2, the valves VV1, VV2, connectors, tubings, etc in the dialysis fluid circuit 12. Thus, it may be desirable to add "compliance" to the dialysis fluid circuit 12, i.e. an ability of the dialysis fluid circuit 12 to expand and contract passively with changes in pressure in the dialysis fluid. Such compliance may be provided by the tubings that define the conduits 19, 20, 21. However, a more controlled compliance may be achieved by installing a compliance chamber in fluid communication with the bypass flow path in the dialysis fluid circuit 12. By ensuring that the compliance chamber is partially filled with dialysis fluid, differences between the flow rates of the pumps P1, P2 will cause dialysis fluid to enter or leave the compliance chamber and thereby reduce the risk for excessive pressures in the dialysis fluid circuit 12. The skilled person realizes that the chambers 26 shown in FIGS. 1, 6 and 7 will provide such compliance in the dialysis fluid circuit 12.

Figure 9:
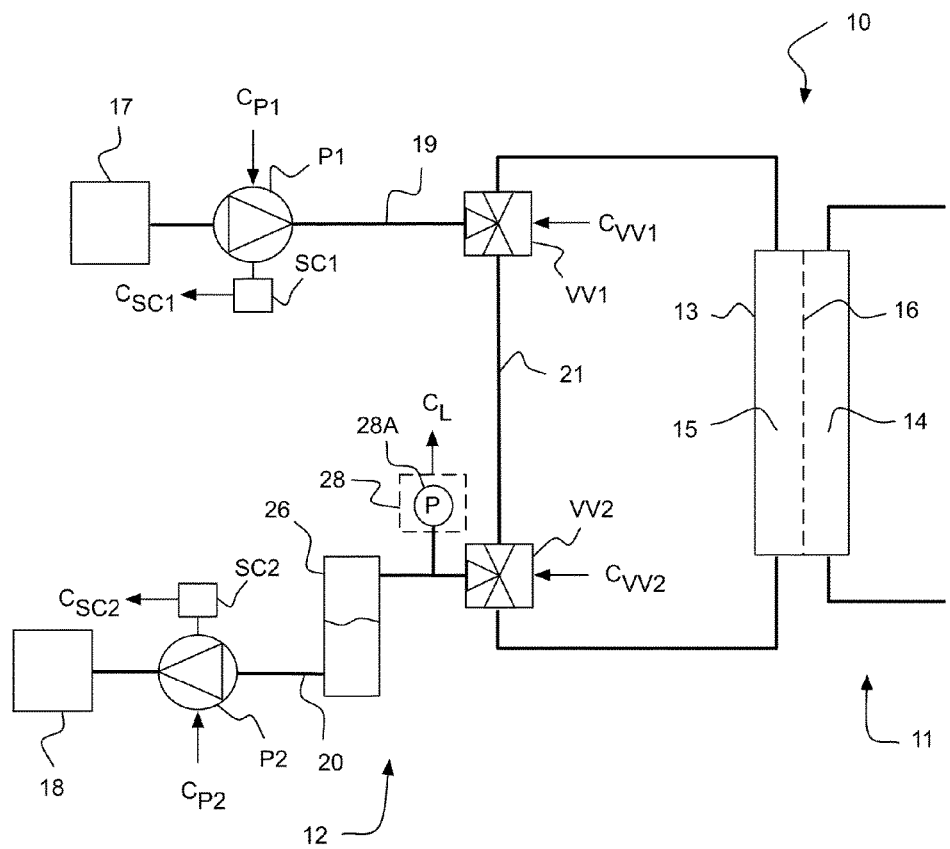

FIG. 9 illustrates another embodiment of a system 10 for ultrafiltration. The system in FIG. 9 differs from the system in FIG. 8 by the provision of a chamber 26, which forms a compliance chamber, and by the location of the pressure sensor 28A in the dialysis fluid circuit 12. The chamber 26 is installed in the inlet conduit 19 between the valve VV2 and the pump P2, and the pressure sensor 28A is arranged to sense the pressure of the dialysis fluid in the inlet conduit 19 between the valve VV2 and the chamber 26. The chamber 26 is sealed to confine a gas (e.g. air) in the space above the dialysis fluid in the chamber 26. Thereby, the pressure measured by the pressure sensor 28A will approximately correspond to the gas pressure in the space above the dialysis fluid. This means that the pressure sensor 28A effectively forms a level sensor 28 and that the sensor signal $C_L$ reflects the level of dialysis fluid in the chamber 26. It is thus realized that the flow rates of the pumps P1, P2 may be balanced, according to step 102 in FIG. 2, based on the sensor signal $C_L$. The skilled person realizes that the pressure sensor 28A may be located in contact with the dialysis fluid anywhere along the bypass flow path, e.g. in the chamber 26, in the outlet conduit 20 between the chamber 26 and the pump P2, in the bypass conduit 21 or in the inlet conduit 19 between the pump P1 and the valve VV1. Alternatively, the pressure sensor 28A may be arranged in direct contact with the gas in the chamber 26, in analogy with FIG. 7. Likewise, the chamber 26 may alternatively be installed in the bypass conduit 21 or in the inlet conduit 19 between the pump P1 and the valve VV1.

In all embodiments disclosed herein, the chamber 26 may be an existing chamber that serves another purpose in a dialysis apparatus. Such an existing chamber may be intermittently switched into fluid communication with the bypass flow path between the pumps P1, P2 during the calibration mode. Alternatively, the chamber 26 may be permanently connected in fluid communication with both the main flow path and bypass flow path. In one example, the chamber 26 is part of a device for removing gas (e.g. carbon dioxide or air) from the dialysis fluid. Taking the embodiment in FIG. 9 as an example, the chamber 26 may thus be part of a conventional gas removal device which is installed in the outlet conduit 20 to remove gases that may be introduced into the dialysis fluid in the dialyzer 13. As included in such a gas removal device, the chamber 26 includes a vent in its top portion which is selectively opened by a dedicated on/off valve (cf. valve VV4 in FIG. 7) for removal of gases that accumulate above the dialysis fluid in the chamber 26. Any such valve is to be closed when the flow rates are balanced during the calibration mode, such that the pressure measured by the pressure sensor 28A represents the gas pressure in the chamber 26 and thus the dialysis fluid level in the chamber 26.

Figure 10:
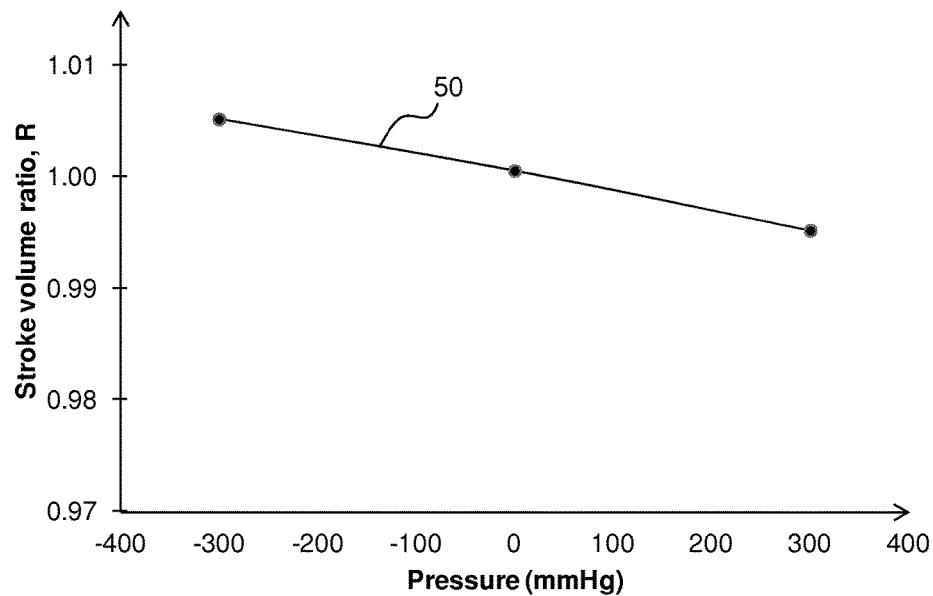
FIG. 10 is a plot of a calibration function relating stroke volume ratio to dialysis fluid pressure measured by the pressure sensor in the system of FIG. 9.

As noted above, the control unit 30 may be configured to determine the relative calibration data for a number of working points of the dialysis fluid circuit 12. These different working points may be given by different pressures measured by the pressure sensor 28A in any of the embodiments shown in FIGS. 7-9, or different levels measured by the level sensor 28 in any of the embodiments shown in FIGS. 1 and 6 provided that the top portion of the chamber 26 is sealed to confine a gas in the space above the dialysis fluid. FIG. 10 is a plot of stroke volume ratios R, acquired according to steps 101-104 in FIG. 2, at three different pressures (working points) measured by the pressure sensor in the embodiment of FIG. 9. Each pair of a working point and a value of the stroke volume ratio forms a data point. The different pressures are established by changing the balanced flow rates generated by the pumps P1, P2 through the bypass flow path. In the example of FIG. 10, a curve 50 has been fitted to the data points, as indicated by a full line. In this particular example, the stroke volume ratio R decreases approximately linearly with increasing pressure. The control unit 30 may be configured to store a calibration function that represents the data in FIG. 10 in the memory 33. The calibration function may be implemented as a data structure, e.g. a table, that associates stroke volume ratios R (or any other type of relative calibration data) with pressure values. Alternatively, the calibration function may be implemented as a mathematical function, linear or non-linear, that represents a factual or estimated relation between stroke volume ratio R (or any other type of relative calibration data) and measured pressure. This relation may correspond to the curve 50 in FIG. 10. In the example of FIG. 9, the control unit 30 may be operable to retrieve the sensor signal $C_L$ also during the treatment mode and thereby measure the current pressure of the dialysis fluid pumped through the dialysis fluid circuit 12. Specifically, in step 203 in FIG. 4, the control unit 30 may access the calibration function 50 based on the current pressure to acquire a corresponding value of the stroke volume ratio R. The control unit 30 then uses this value of the stroke volume ratio R to set the speeds of the pumps P1, P2, e.g. according to steps 204-206 in FIG. 4. This adaptation of the stroke volume ratio R may be done at any time interval during the treatment mode. The adaptation presumes that the pressure is measurable during both the calibration mode and the treatment mode. Thus, the pressure sensor 28A is suitably located to be included in both the bypass flow path and the main flow path, e.g. as shown in FIG. 9.

The control unit 30 may be operable to generate and store the calibration function during manufacture of the system 10, so that the calibration function is available for retrieval when the system 10 is subsequently operated in the treatment mode 200. Suitably, the calibration function is generated based on stroke volume ratios R for at least three different pressures, which are well-distributed within the normal range of operating pressures for the treatment mode 200. The control unit 30 may be further operable to execute the calibration mode 100 for re-generation of the calibration function whenever there is a change to the configuration of the system 10, e.g. during service and maintenance. The re-generated calibration function is stored in memory 33. In the following, the generation of the calibration function is referred to as "service calibration". It is conceivable to execute the service calibration more frequently, e.g. at start-up of the system 10 in preparation of each treatment. The service calibration results in a new calibration function being generated and stored in the system 10, e.g. in memory 33.

In one embodiment, the control unit 30 is configured to execute the calibration mode 100 for validation of the system 10 in preparation of each treatment, and possibly at one or more time points during the treatment. In the following, this validation process is denoted "treatment calibration". The treatment calibration is executed for the purpose of verifying that the stored calibration function adequately represents the system 10 and, if necessary, updating the calibration function, which suitably is implemented as a mathematical function and stored in the memory 33. Both the service calibration and the treatment calibration involves establishing the bypass flow path, controlling the pumps P1, P2 to balance their flow rates, and computing the relative calibration data based on the pump speeds. The treatment calibration differs from the service calibration in that it does not determine a sufficient number of data points to completely re-generate the calibration function, but rather determines one data point, or at least no more than a few different data points, to be used for validation based on an existing calibration function. Thereby, the treatment calibration is more time and processing efficient than the service calibration.

The rationale for performing the treatment calibration is that the relation between the stroke volumes of the pumps P1, P2 may change during use of the system 10, e.g. as a result of wear and deterioration of the pumps P1, P2, changes in the pressure of the fresh dialysis fluid supplied by the source 17, changes to the main flow rate $Q_{MAIN}$, changes in the flow resistance of the receptacle 18, etc. Generally, any change of an operating parameter that affects the pressures at the inlet and outlet of the respective pump P1, P2 may cause a change in the stroke volume ratio.

It may be advantageous to perform the treatment calibration at start-up of the system 10 in preparation of each treatment and/or at one or more time points during each treatment, to ensure that the stored calibration function is representative for the system 10. This will increase the accuracy and robustness of the UF control. The treatment calibration may be governed by pre-scheduling or requested by control logics, or a combination thereof. Such control logics may initiate a treatment calibration whenever one or more specific operating parameters of the system 10 are changed, e.g. the main flow rate $Q_{MAIN}$, the temperature of the fresh dialysis fluid, the UF rate $Q_{UF}$, etc. The pre-scheduling may include an early treatment calibration (e.g. 5-15 minutes into treatment) followed by fixed or increasing intervals between subsequent treatment calibrations.

Increasing the number of treatment calibrations during the treatment may be an option to achieve a higher UF accuracy, e.g. in the case of pediatric or acute treatments.

Figure 11:
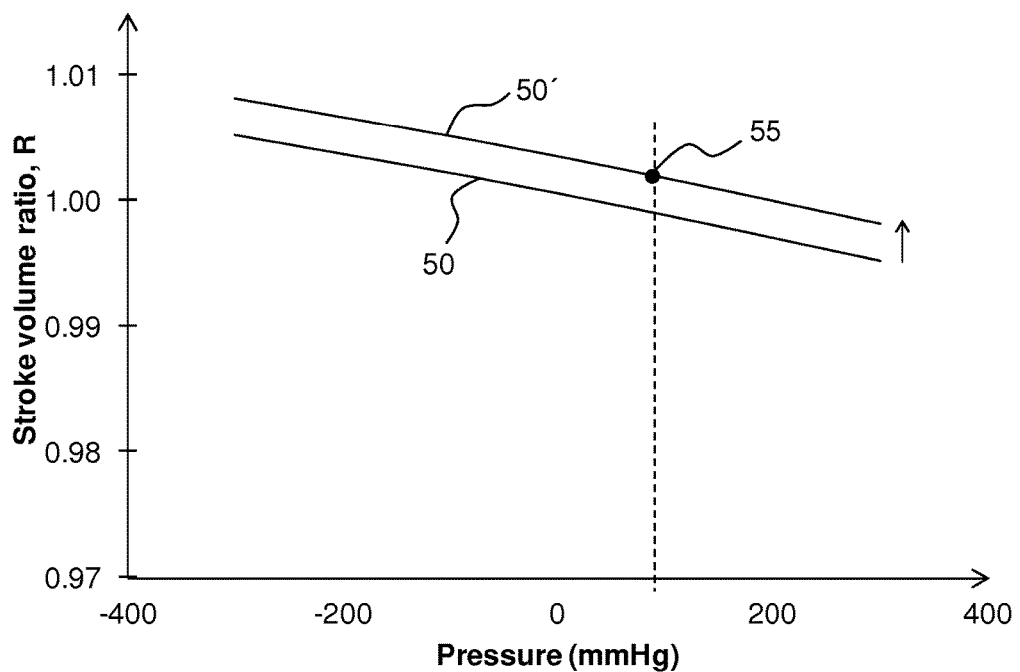
FIG. 11 illustrates adjustment of the calibration function as result of a treatment calibration.

During the treatment calibration, the control unit 30 calculates a stroke volume ratio R (relative calibration data) for a validation working point, which is defined by a measured pressure or a measured level in the chamber 26 (if present). The control unit 30 then retrieves the calibration function from memory 33, and adjusts parameters of the calibration function such that it matches the acquired data point, i.e. the calculated stroke volume ratio R and the measured pressure/level. For example, as shown in FIG. 11, the stored calibration function, represented by the curve 50, may be translated in the vertical direction such that the acquired data point 55 falls on the curve. Such an adjusted calibration function 50' may be generated by adding an offset value to the calibration function 50, the offset value being computed as the difference between the calculated ratio R at the validation working point (i.e. the ratio R obtained by the treatment calibration) and the output value of the calibration function 50 at the validation working point. The control unit 30 then uses the adjusted calibration function 50' for UF control, at least in the subsequent treatment mode.

In one implementation, the control unit 30 stores the adjusted calibration function 50' in memory 33 to replace the calibration function 50. Thus, in this implementation the adjusted calibration function 50' is accessed based on the current pressure to acquire a corresponding value of the stroke volume ratio for UF control (cf. step 203 in FIG. 2) and is assumed to correctly represent the system 10 until another service calibration is performed or until another adjusted calibration function 50' is obtained by a forthcoming treatment calibration. In this implementation, the treatment calibration will validate the system 10 against the latest calibration function 50, 50', be it obtained by a service calibration or a previous treatment calibration.

In another implementation, the control unit 30 stores, in memory 33, both the calibration function 50 obtained by the latest service calibration and the adjusted calibration function 50' obtained by the latest treatment calibration. In this implementation, the adjusted calibration function 50' is used temporarily for UF control in the subsequent treatment mode (cf. step 203 in FIG. 2), until the control unit 30 initiates another treatment calibration or terminates the current treatment session. The calibration function 50 obtained by the latest service calibration is used as a master or reference, and each treatment calibration is implemented to validate the system 10 against this calibration function 50. Similarly, at start-up of the system 10, the control unit 30 will retrieve the calibration function 50 and use it for UF control.

Figure 12:
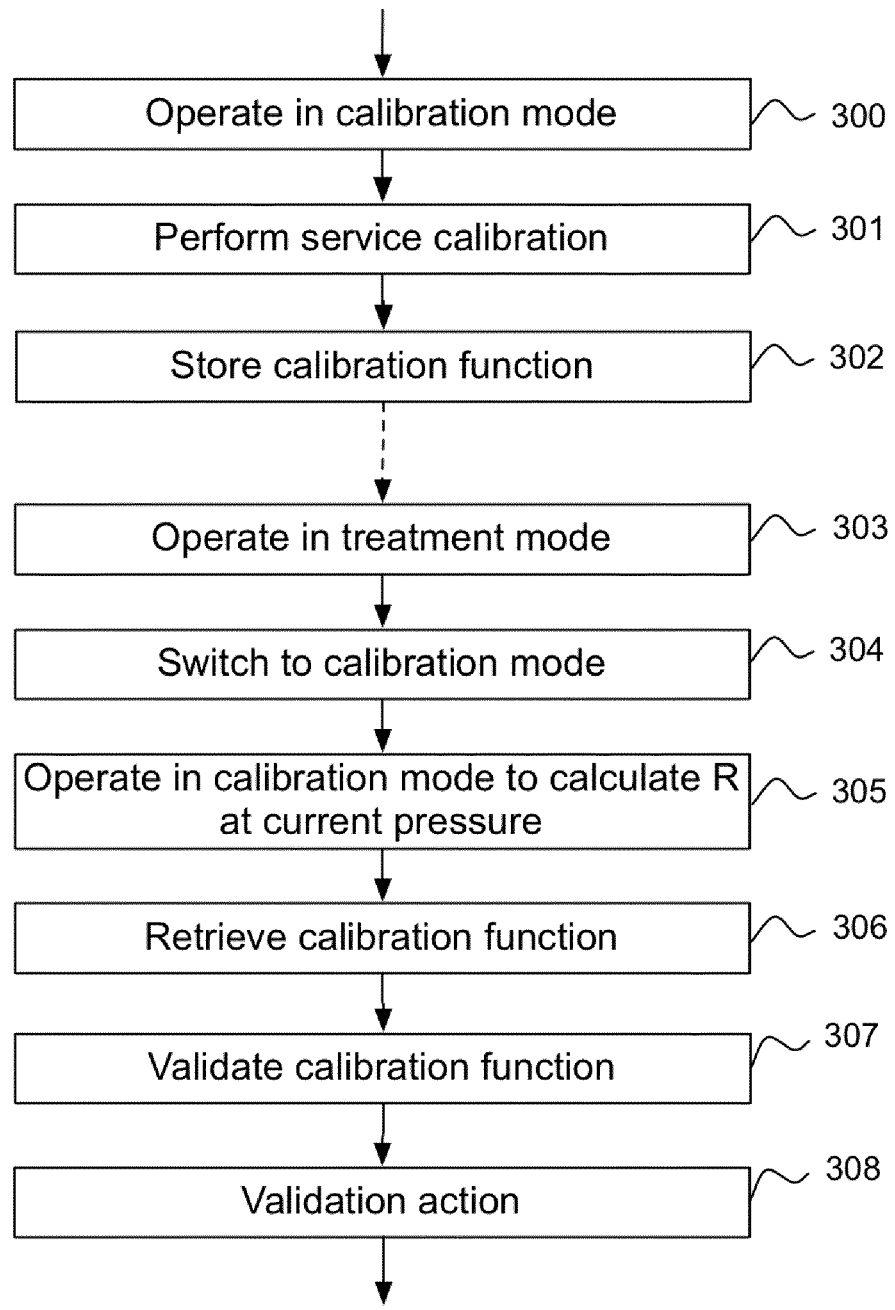
FIG. 12 is a flow chart of a process for achieving the adjustment in FIG. 11.

The service and treatment calibrations are further exemplified in FIG. 12, in which all steps are performed by the control unit 30. In step 300, the system 10 is set to operate in the calibration mode. In step 301, a service calibration is executed, e.g. according to steps 101-104 in FIG. 2 at a number of different pressures, and a calibration function is generated. In step 302, the calibration function is stored, e.g. in memory 33. Some time later (indicated by dashed arrow in FIG. 12), the treatment calibration is performed. In the illustrated example, the system 10 is operated in the treatment mode (step 303) and switched to the calibration mode (step 304) for execution of a treatment calibration, e.g. according to steps 101-103 in FIG. 2, at a current pressure measured by the pressure sensor (28A in FIG. 9). The treatment calibration (step 305) results in a calculated stroke volume ratio R for the current pressure, which defines a validation working point. In principle, the treatment calibration may be executed at any current pressure, as measured by the sensor 28A. However, it may be advantageous for the validation working point to be similar or identical to an actual working point for the system 10 during the treatment mode(s), such that the pumps P1, P2 operate at reasonably similar conditions during the treatment calibration and the treatment mode. Thus, the control unit 30 may actively control one or more of the pumps P1, P2 to achieve a pressure (at sensor 28A) which is essentially the same as the pressure (at sensor 28A) during the preceding treatment mode (cf. step 303). In one practical embodiment, the pumps P1, P2 are furthermore controlled to maintain the main flow rate $Q_{MAIN}$ used in the preceding treatment mode (cf. step 303), recalling that it may be desirable to avoid momentary changes to $Q_{MAIN}$ at least for certain designs of the source 17.

Returning to the flow chart in FIG. 3, the calibration function is retrieved from memory 33 in step 306 and the system 10 is then validated in step 307 using the calculated stroke volume ratio R from step 305. The validation may involve calculating the above-mentioned offset value and comparing it to one or more thresholds. In step 308, the control unit 30 takes action depending on the outcome of the validation in step 307. For example, if the offset value exceeds a first threshold, the control unit 30 may issue an alarm and cause the system 10 to enter a fail safe state. If the offset value is below a second threshold, which is lower than the first threshold, the control unit 30 may refrain from adjusting the stored calibration function. If the offset value lies between the first and second thresholds, the control unit 30 may adjust the calibration function and store the adjusted calibration function in memory, e.g. as described in relation to FIG. 11. In a variant, only the first threshold is used in the validation, which thus aims at identifying an alarm condition. In a further variant, only the second threshold is used in the validation, which thus aims at identifying a need for adjustment of the calibration function. After step 308, unless an alarm condition has been identified, the control unit 30 will return to the treatment mode. As noted above, steps 304-308 may be executed more than once during a treatment.

It is to be understood that shifting the calibration function by the offset value, as described above and illustrated in FIG. 11, generally improves the accuracy of the UF control. In practice, the true calibration function may deviate from the shifted calibration function, especially at pressures far away from the current pressure used in the treatment calibration (cf. data point 55 in FIG. 11). Furthermore, the data point 55 is correct for the pressures that are present at the inlets and outlets of the pumps P1, P2 during the treatment calibration. If one or more of these pressures differ significantly when the system 10 is switched between the main flow path and the bypass flow path, the data point will not be entirely correct during the treatment, and the shifted curve will be less accurate.

In one embodiment, errors caused by varying pressure conditions around the pumps between the calibration and treatment modes are reduced by computing a compensation value as a function of a set of operating parameters for the system 10. The set of operating parameters estimates the changes in the pressures at the inlets and outlets of the pumps P1, P2 when switching between the calibration and treatment modes. At lest part of these operating parameters may be measured in the system 10, while others may be estimated from set values for the system 10. In the following discussion, the pressures at the inlet and outlet of the upstream pump P1 are denoted $p_1$ and $p_2$, respectively, and the pressures at the inlet and outlet of the downstream pump P2 are denoted $p_3$ and $p_4$, respectively.

The following linear compensation function may be used:

$$R'=R+(c_{\Delta p1}\times\Delta p1)+(c_{\Delta p2}\times\Delta p2)+(c_{\Delta p3}\times\Delta p3)+(c_{\Delta p4}\times\Delta p4) \quad (9)$$

In the compensation function, R' is the compensated ratio, R is the ratio that is obtained for a current pressure during a treatment mode, by use of data obtained in a calibration mode, the differential parameters $\Delta p1$, $\Delta p2$, $\Delta p3$ and $\Delta p4$ represent differences in pressure $p_1$, $p_2$, $p_3$ and $p_4$, respectively, between the calibration mode and the treatment mode, and $c_{\Delta p1}$, $c_{\Delta p2}$, $c_{\Delta p3}$ and $c_{\Delta p4}$ are compensation factors. The compensation factors may be determined empirically or theoretically. The ratio R may be obtained in any of the ways described hereinabove. Thus, the ratio R may be given as an output value of a calibration function 50, 50' which has been obtained during the calibration mode. Alternatively, if the system 10 is controlled such that the working point (pressure) is the same during treatment calibration and during the treatment mode, the ratio R may be obtained by performing a treatment calibration at the current pressure.

In one embodiment, the system 10 is provided with pressure sensors (not shown) that measure all of the pressures $p_1$, $p_2$, $p_3$ and $p_4$. Based on this data, Eq. (9) yields a compensated ratio R' for a given ratio R.

In another embodiment, assumptions are made to reduce the cost and complexity of evaluating the compensation function.

One assumption may be that the pressure $p_1$ is invariant between the calibration and treatment modes, i.e. $\Delta p1=0$. This assumption is valid at least if the main flow rate $Q_{MAIN}$ is the same or similar in these modes.

Another assumption is that the pressure $p_3$ is invariant between the calibration and treatment modes. This assumption presumes that the control unit 30 maintains (substantially) the same working point between the treatment mode and the calibration mode (treatment calibration), as described above. The pressure $p_3$ in the treatment mode is governed by the pressures on the blood side (inlet and outlet of the dialyzer 13) and the flow conditions through the dialyzer 13 on the dialysis fluid side (through flow rates $Q_1$ and $Q_2$). As long as the main flow rate, $Q_{MAIN}$, and the UF rate, $Q_{UF}$, are constant during the treatment mode, the pressure $p_3$ will only change if the ultrafiltration coefficient changes (for example as a consequence of a clotted dialyzer). It is also assumed that the variations in pressure $p_3$ during the treatment mode will be compensated for by the calibration function. Under these assumptions, the compensation function need not compensate for the pressure difference $\Delta p3$. Otherwise, compensation for $\Delta p3$ is straightforward since the pressure $p_3$ may be given by, or at least estimated from, the pressure readings of the sensor 28A.

Another assumption is based on the fact that the pressure $p_4$ will decrease when switching from the treatment mode to the calibration mode since the fluid flow rate generated by the pump P2 will decrease with the size of the UF rate $Q_{UF}$, thus lowering the flow resistance in the drain path downstream of the pump P2. Tests show that the pressure difference $\Delta p4$ correlates strongly with ultrafiltration. Hence, it is assumed that $Q_{UF}$ may be used instead of $\Delta p4$ in the compensation function.

In total, these assumptions yield the following simplified compensation function:

$$R'=R+(c_{\Delta p2}\times\Delta p2)+(c_{\Delta p4}\times Q_{UF}) \quad (10)$$

It should be noted that the UF rate $Q_{UF}$ may be a small quantity in many dialysis settings. Hence, the pressure difference $\Delta p4$ may have a minor impact on the accuracy of the ratio R. Under such circumstances, the compensation function need not compensate for the pressure difference $\Delta p4$.

When applying the compensation function, the present applicant has surprisingly found that a small error may persist between the set value $Q_{UF}$ and the actual UF rate $Q_{UF\_real}$. This UF error has been found to correlate with the main flow rate $Q_{MAIN}$. A corresponding compensation term may therefore be added to the compensation function according to Eq. (10):

$$R'=R+(c_{\Delta p2}\times\Delta p2)+(c_{\Delta p4}\times Q_{UF})+(c_{MAIN}\times Q_{main}) \quad (11)$$

where $c_{MAIN}$ is an empirically determined compensation factor. A corresponding compensation term may be added to the compensation function according to Eq. (9). It is realized that the dependence on $Q_{MAIN}$ may alternatively be overcome by calculating the ratio R in a service or treatment calibration, in which $Q_{MAIN}$ is the same as in the treatment mode.

Depending on the configuration and operation of the system 10, the compensation function may differ from examples described above. For example, the pressure differentials may be included in any combination in the compensation function, or only one of the pressure differentials may be included. Furthermore, other functional relations, linear or non-linear, between the ratio R (or any other type of relative calibration data) and the pressure differential(s) are conceivable.

Figure 13:
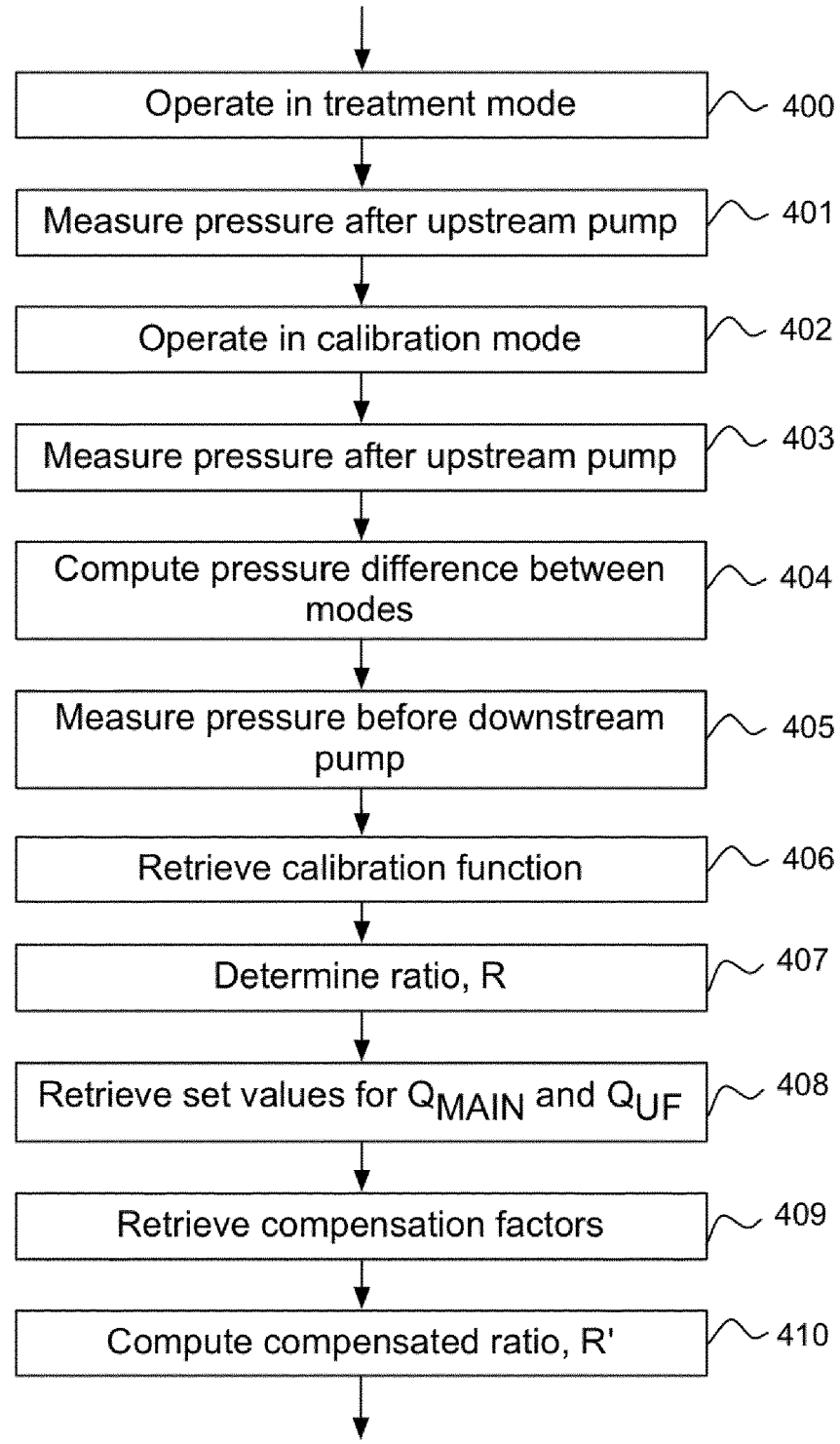
FIG. 13 is a flow chart of a process for compensating a stroke volume ratio for pressure variations between calibration and treatment modes.

The use of a compensation function will be further described with reference to the flow chart in FIG. 13. in which all steps are performed by the control unit 30. The system 10 is operated in the treatment mode (step 400), and the pressure $p_2$ at the outlet of the upstream pump P1 is measured or estimated based on the output of a pressure sensor (step 401). This pressure sensor is not shown in the drawings, but may be arranged to measure the pressure in the inlet conduit 19 between the pump P1 and the first valve VV1. In one implementation (not shown), the pressure sensor 28A is connected for fluid communication with both the compliance chamber 26 and inlet conduit 19, via a respective control valve. Thereby, the pressure sensor 28A is operable to measure either of the pressures $p_2$, $p_3$, by the control unit 30 selectively opening one of these control valves. This implementation saves the cost of one pressure sensor. The system 10 is then set to operate in the calibration mode (step 402), the pressure $p_2$ at the outlet of the upstream pump P1 is again measured or estimated, and the pressure difference $\Delta p2$ is computed. The pressure $p_3$ at the inlet of the pump P2 is also measured (step 405). The calibration function is retrieved from memory (step 406) and using the calibration function, the ratio R is obtained for the measured pressure $p_3$ (step 407). The set values for the main flow rate, $Q_{MAIN}$, and the UF rate, $Q_{UF}$, are acquired, if not already available (step 408), and the relevant compensation factors are retrieved from memory (step 409). Finally, in step 410, the compensated stroke volume ratio R' is computed using Eq. (11).

Figure 14:
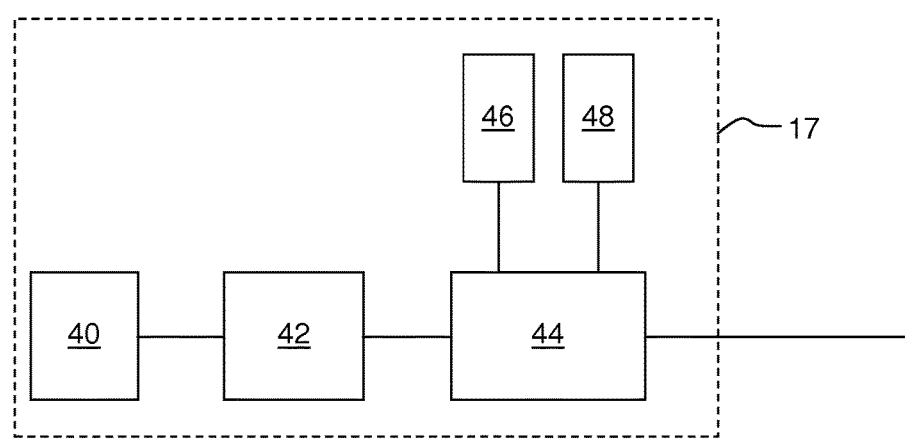
FIG. 14 is a block diagram of a source of fresh dialysis fluid for use in embodiments of the invention.

FIG. 14 illustrates a source 17 which is configured to prepare the fresh dialysis fluid by mixing concentrates with water. Block 40 is a water inlet that supplies water to a conditioning block 42, which may be configured to heat the incoming water to a predefined temperature and remove gaseous substances, e.g. air, from the incoming water. The conditioned water is supplied to a mixing block 44, which is configured to mix the water with at least two different concentrates, supplied from containers 46, 48, to produce the fresh dialysate fluid which is pumped into the inlet conduit 19 by the pump P1 (see e.g. FIG. 1). For hemodialysis, one of the concentrates may contain sodium bicarbonate $NaHCO_3$. Tests have revealed that the ratios R measured during a service calibration in a system 10 having this type of source 17 are slightly incorrect. After significant experimentation, the present Applicant found the cause of the error to be a carbon dioxide ($CO_2$) fluid/gas equilibrium process. Before the $NaHCO_3$ dosing begins, virtually no $CO_2$ is present in the flow path between the pumps. As the dosing begins, the following (simplified) reactions occur:

$$NaHCO_3+CH_3COOH\longleftrightarrow CH_3COONa+H_2CO_3(l)+$$
$$CO_2(l) \quad H_2CO_3(l)\longleftrightarrow CO_2(l)\longleftrightarrow CO_2(g)$$

This means that carbonic acid and $CO_2$ in the fresh dialysis fluid will have a corresponding equilibrium partial pressure in the gas phase. Whether this equilibrium partial pressure is achieved or not depends on the contact time, the contact surface and flow conditions. When the fresh dialysis fluid containing $CO_2$ enters the compliance chamber 26, $CO_2$ will be released from the dialysis fluid so that it moves towards the equilibrium partial pressure of $CO_2$. Thereby, the compliance gas mass (and hence the total pressure between the pumps P1, P2) will increase until equilibrium is reached. If pressure control is active during the calibration mode, the pump P2 will increase its rotational speed in order to keep the pressure/level constant in the compliance chamber 26. If the speed $n2_c$ of the pump P2 is determined before equilibrium is reached, the calculated stroke volume ratio R will be incorrect. One solution to this problem is to use a long stabilization time at each pressure set point during the service calibration. To reduce the total time for the service calibration, the control unit 30 may instead be configured to disable the dosing of sodium bicarbonate into the mixing block 44 during the service calibration.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For example, the system for ultrafiltration may include more than one upstream pump and/or more than one downstream pump. The relative calibration data may be determined for these pumps as described herein, by establishing the bypass flow path between pairs of upstream and downstream pumps and performing steps 102-105 for each pair of upstream and downstream pumps.

The upstream and downstream pumps are volumetric pumps and maybe implemented as either piston pumps or diaphragm (membrane) pumps. It is to be understood that the upstream and downstream pumps may have different nominal stroke volumes. It is also possible that the upstream and downstream pumps are of different designs or types.

The skilled person also realizes that there are alternatives to using a pressure sensor or a level sensor for balancing the flow rates of the pumps during the calibration mode. For example, the level sensor 28 in FIG. 1 may be replaced by simple flow sensor that measures the flow of dialysis fluid in the connecting conduit 27 when the dialysis fluid circuit 12 is set to establish the bypass flow path. The control unit 30 may adjust the frequency of one or both pumps P1, P2 until the output signal of the flow meter indicates that the flow rate in the connecting conduit 27 is zero.

Even if it is possible to use the pressure sensor 28A to both identify an invariant level in the compliance chamber 26 and to determine a pressure representative of a working point of the system 10, it is quite possible to implement the system 10 with separate devices for determining level and pressure. As noted above, the pressure of the working points need not be determined at the location of the compliance chamber 26, but may in principle be determined anywhere within the dialysis fluid circuit 12. If the pressure is measured in the inlet conduit 19 between the pump P1 and the valve VV1, Equations (9)-(11) are modified by replacing $p_2$ with $p_3$ and $\Delta p2$ with $\Delta p3$. It is also to be noted that Equations (9)-(11) are also applicable if the set value $Q_{MAIN}$ represents the flow of dialysis fluid out of the dialyzer 13 and the UF rate is controlled by adjusting the speed of the upstream pump P1. Furthermore, is may be noted that the compliance chamber 26 may instead be located in fluid communication with the inlet conduit 19 upstream of the first valve VV1.

In the foregoing description, the control unit 30 controls the UF rate exclusively by setting the speeds of the upstream and downstream pumps, using the relative calibration data obtained in the calibration mode, to achieve a desired difference in the flow rates between the upstream and downstream pumps. In an alternative embodiment, the control unit 30 sets the flow rates of the upstream and downstream pumps equal, using the relative calibration data obtained in the calibration mode, and controls the UF rate by operating a dedicated UF pump ("filtration pump"), which is connected to the outlet conduit 20 between the downstream pump P2 and the dialyzer 13, as is well-known in the art and described in the Background section. It is also conceivable to configure the control unit 30 to set the UF rate by a combination of controlling a separate UF pump and controlling the difference in flow rates between the upstream and downstream pumps.

The invention claimed is:
1. A dialysis apparatus, comprising:
  a dialyzer;
  a dialysis fluid distribution system connected for fluid communication with the dialyzer and comprising a first pump and a second pump, the dialysis fluid distribution system being operable to selectively establish a main flow path that extends between the first and second pumps via the dialyzer, and a bypass flow path that bypasses the dialyzer and extends between the first and second pumps; and
  a control unit electrically connected to the dialysis fluid distribution system and configured to control a respective frequency of the first and second pumps, wherein the first and second pumps are configured to generate a respective flow rate by repeatedly discharging, at the respective frequency, a respective stroke volume of dialysis fluid;
  wherein the control unit is configured to, in a calibration mode,
    (i) operate the dialysis fluid distribution system to establish the bypass flow path,
    (ii) control the first pump to operate at a first calibration frequency and the second pump to operate at a second calibration frequency so as to balance the flow rates generated by the first and second pumps, and
    (iii) determine relative calibration data that represents a relation between the stroke volumes of the first and second pumps based on the first and second calibration frequencies; and wherein the control unit is configured to, in a treatment mode,
(i) operate the dialysis fluid distribution system to establish the main flow path,
(ii) assign a predefined nominal stroke volume to the first pump,
(iii) set a respective treatment frequency of the first pump to generate, based on the predefined nominal stroke volume of the first pump, a first flow rate of dialysis fluid,
(iv) set a respective treatment frequency of the second pump to generate a second flow rate of dialysis fluid that differs from the first flow rate by a selected ultrafiltration rate, and
(v) control the first and second pumps, based on the relative calibration data, to operate at the respective treatment frequencies of the first and second pumps to generate the selected ultrafiltration rate in the dialyzer.

2. The dialysis apparatus of claim 1, wherein, in the treatment mode, a stroke volume of the second pump is set to generate the second flow rate based on the predefined nominal stroke volume of the first pump.

3. The dialysis apparatus of claim 1, wherein the control unit is configured to set the respective treatment frequencies of the first and second pumps such that one of the first or second flow rates is equal to a selected flow rate of dialysis fluid out of or into the dialyzer.

4. The dialysis apparatus of claim 3, wherein the control unit is further configured to receive a first set value that represents the selected flow rate of dialysis fluid out of or into the dialyzer, and a second set value that represents the selected ultrafiltration rate.

5. The dialysis apparatus of claim 1, wherein the control unit, in the treatment mode, is configured to set the respective treatment frequencies of the first and second pumps according to:

$$\begin{cases} n1 = \frac{Q1}{S1_n} \\ n2 = \frac{Q2}{S1_n} \cdot \frac{n2_c}{n1_c} \end{cases}$$

wherein n1 is the respective treatment frequency of the first pump, Q1 is the first flow rate of dialysis fluid generated by the first pump, $S1_n$ is the nominal stroke volume assigned to the first pump, n2 is the respective treatment frequency of the second pump, Q2 is the second flow rate of dialysis fluid generated by the second pump, $n1_c$ is the first calibration frequency, and $n2_c$ is the second calibration frequency, and wherein the absolute difference between Q1 and Q2 is equal to the selected ultrafiltration rate.

6. The dialysis apparatus of claim 1, wherein said relation between the stroke volumes of the first and second pumps is equal to the inverse of the relation between the first and second calibration frequencies.

7. The dialysis apparatus of claim 1, wherein the control unit is further configured to, in the calibration mode, store the relative calibration data in an electronic memory for subsequent retrieval by the control unit in the treatment mode.

8. The dialysis apparatus of claim 1, wherein the dialysis fluid distribution system further comprises a flow difference meter configured to generate an output signal representative of a difference between the flow rates generated by the first and second pumps, wherein the control unit is operable, in the calibration mode, to balance the flow rates generated by the first and second pumps based on the output signal of the flow difference meter.

9. The dialysis apparatus of claim 8, wherein the flow difference meter comprises a pressure sensor arranged to sense a pressure of the dialysis fluid in the dialysis fluid distribution system, and wherein the output signal represents said pressure.

10. The dialysis apparatus of claim 8, wherein the bypass flow path is connected in fluid communication with a chamber in the dialysis fluid distribution system, wherein the flow difference meter comprises a level detector, which is arranged to generate the output signal to indicate at least one level of dialysis fluid in the chamber, and wherein the control unit is operable, in the calibration mode, to balance the flow rates between the first and second pumps by generating a stabilized level of dialysis fluid in the chamber as indicated by the output signal.

11. The dialysis apparatus of claim 10, wherein the level detector is configured to indicate a range of levels of dialysis fluid in the chamber.

12. The dialysis apparatus of claim 10, wherein the level detector comprises a pressure sensor which is arranged to sense a pressure in the dialysis fluid distribution system such that an invariant pressure indicates that the level of dialysis fluid is stabilized in the chamber.

13. The dialysis apparatus of claim 12, wherein a top portion of the chamber contains a gas and is sealed during the calibration mode, wherein the pressure sensor is configured to generate the output signal to represent the pressure of the gas in the chamber.

14. The dialysis apparatus of claim 9, wherein the pressure sensor is arranged to be included in both the bypass flow path and the main flow path.

15. The dialysis apparatus of claim 12, wherein the pressure sensor is connected to the chamber so as to sense a hydrostatic pressure of the dialysis fluid in the chamber.

16. The dialysis apparatus of claim 1, wherein the control unit is configured to, in the calibration mode, operate the first and second pumps to balance the flow rates of dialysis fluid at different working points of the dialysis fluid distribution system; determine the relative calibration data for each of the different working points; and generate a calibration function that relates the relative calibration data to the different working points; and wherein the control unit is configured to, in the treatment mode at a current working point of the dialysis fluid distribution system, obtain current relative calibration data by use of the calibration function and the current working point; and control the first and second pumps, based on the current relative calibration data, to operate at the respective treatment frequency so as to generate a selected ultrafiltration rate in the dialyzer.

17. The dialysis apparatus of claim 16, wherein the control unit is configured to identify the different working points and the current working point based on an output signal from a pressure sensor arranged to sense a pressure of the dialysis fluid in the dialysis fluid distribution system.

18. The dialysis apparatus of claim 16, wherein the control unit is configured to (i) validate the dialysis fluid distribution system, and (ii) operate the dialysis fluid distribution system to (a) establish the bypass flow path, (b) control the first and second pumps to balance their flow rates at a validation working point of the dialysis fluid distribution system, (c) determine the relative calibration data for the validation working point, and (d) validate the dialysis fluid distribution system by comparing the relative calibration data for the validation working point with an output value of the calibration function at the validation working point.

19. The dialysis apparatus of claim 18, wherein the control unit is configured to take dedicated action based on a difference between the relative calibration data for the validation working point and the output value, said dedicated action comprising at least one of: initiating an alarm, and adjusting the calibration function.

20. The dialysis apparatus of claim 19, wherein the control unit is configured to adjust the calibration function by adding the difference to the calibration function.

21. The dialysis apparatus of claim 16, wherein the control unit is configured to obtain the current relative calibration data by retrieving a current output value of the calibration function at the current working point and compensate the current output value for one or more estimated or measured pressure differences within the dialysis fluid distribution system between the treatment mode and the calibration mode.

22. The dialysis apparatus of claim 21, wherein the one or more pressure differences relate to at least one of: an inlet of the first pump, an outlet of the first pump, an inlet of the second pump, and an outlet of the second pump.

23. The dialysis apparatus of claim 1, wherein the control unit is configured to, during the treatment mode, operate a source to generate dialysis fluid by dosing a concentrate into water, said concentrate comprising sodium bicarbonate, and wherein the control unit is configured to, during the calibration mode, disable the dosing of said concentrate into the water.

24. The dialysis apparatus of claim 1, wherein the control unit, in the calibration mode, is configured to assign a respective predefined nominal stroke volume to the first and second pumps, operate the first and second pumps at a first and a second start frequency, respectively, such that the first start frequency multiplied by the predefined nominal stroke volume of the first pump is essentially equal to the second start frequency multiplied by the predefined nominal stroke volume of the second pump, and modify at least one of the first and second start frequencies until the flow rates of dialysis fluid generated by the first and second pumps are balanced.

25. The dialysis apparatus of claim 1, wherein each of the first and second pumps comprises a respective pulse generator arranged to generate one or more pulses for each stroke volume displaced by the first and second pump, respectively, and wherein the control unit, in the calibration mode, is configured to represent the first and second calibration frequencies by a first number of pulses and a second number of pulses, respectively, generated by the respective pulse generator during a test period while the flow rates of dialysis fluid generated by the first and second pumps are balanced.

26. The dialysis apparatus of claim 1, wherein the first pump is located upstream of the dialyzer in the main flow path and the second pump is located downstream of the dialyzer in the main flow path.

27. The dialysis apparatus of claim 1, wherein each of the first and second pumps is one of a diaphragm pump and a piston pump.

* * * * *